(12) United States Patent
Lee et al.

(10) Patent No.: US 12,301,014 B2
(45) Date of Patent: May 13, 2025

(54) METHOD AND APPARATUS WITH WIRELESS POWER RECEPTION, WIRELESS COMMUNICATION, AND ELECTRICAL STIMULATION

(71) Applicant: Samsung Electronics Co., Ltd., Suwon-si (KR)

(72) Inventors: Jaechun Lee, Seoul (KR); Chisung Bae, Yongin-si (KR); Sang Joon Kim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 427 days.

(21) Appl. No.: 17/398,269

(22) Filed: Aug. 10, 2021

(65) Prior Publication Data

US 2022/0320906 A1    Oct. 6, 2022

(30) Foreign Application Priority Data

Mar. 31, 2021  (KR) .......................... 10-2021-0041908

(51) Int. Cl.
*H02J 50/12*  (2016.01)
*H04B 5/79*  (2024.01)
(Continued)

(52) U.S. Cl.
CPC ............... *H02J 50/12* (2016.02); *H04B 5/79* (2024.01); *A61B 5/6868* (2013.01); *A61N 1/3787* (2013.01); *H02J 2310/23* (2020.01)

(58) Field of Classification Search
CPC .... H02J 50/12; H02J 2310/23; H04B 5/0037; A61B 5/6868; A61N 1/3787
See application file for complete search history.

(56) References Cited

U.S. PATENT DOCUMENTS 6,164,532 A * 12/2000 Suga ........................ H02J 50/80
                                                            235/375
7,672,731 B2    3/2010 Dublin et al.
(Continued)

FOREIGN PATENT DOCUMENTS

| JP | 2007-505653 A | 3/2007 |
|---|---|---|
| JP | 4699097 B2 | 6/2011 |
| WO | WO 2021/009646 A1 | 1/2021 |

OTHER PUBLICATIONS

Extended European search report issued on Nov. 8, 2022, in counterpart European Patent Application No. 21211325.2 (12 pages in English).

(Continued)

*Primary Examiner* — Daniel Cavallari
*Assistant Examiner* — Brian K Baxter
(74) *Attorney, Agent, or Firm* — NSIP Law

(57) ABSTRACT

An electronic apparatus includes: an external coil connected via a pair of a first feed-through portion and a second feed-through portion to a communication circuit, the external coil comprising a first coil part and a second coil part disposed outside a housing; a wireless power transmission circuit; an electrode signal processing circuit included in the housing; an external capacitor disposed outside the housing and connected between the first coil part and the second coil part; a first electrode connected to the first coil part at one end of the external capacitor; and a second electrode connected to the second coil part at another end of the external capacitor.

24 Claims, 19 Drawing Sheets

(51) Int. Cl.
*A61B 5/00* (2006.01)
*A61N 1/378* (2006.01)

(56) References Cited

U.S. PATENT DOCUMENTS

| | | | |
|---|---|---|---|
| 8,742,623 B1 | 6/2014 | Biederman et al. | |
| 9,463,320 B2 | 10/2016 | Imran et al. | |
| 10,238,872 B2 | 3/2019 | Pivonka et al. | |
| 2006/0085041 A1* | 4/2006 | Hastings | A61N 1/37223 607/33 |
| 2008/0081631 A1 | 4/2008 | Rofougaran | |
| 2009/0015075 A1* | 1/2009 | Cook | H04B 5/0037 307/149 |
| 2010/0191311 A1* | 7/2010 | Scheiner | A61B 5/4047 607/66 |
| 2010/0211172 A1* | 8/2010 | Bellamkonda | A61B 5/0031 607/116 |
| 2011/0043050 A1* | 2/2011 | Yabe | H02J 50/70 307/104 |
| 2011/0248673 A1* | 10/2011 | Aerts | H02J 7/0044 320/108 |
| 2013/0079847 A1* | 3/2013 | Keuninckx | A61N 1/40 607/57 |
| 2014/0094674 A1 | 4/2014 | Nurmikko et al. | |
| 2014/0191819 A1* | 7/2014 | Suzuki | H01F 38/14 333/17.3 |
| 2015/0263531 A1* | 9/2015 | Kozakai | H02J 50/12 307/104 |
| 2015/0311881 A1* | 10/2015 | Nagumo | H01Q 1/50 343/861 |
| 2015/0365139 A1* | 12/2015 | Moon | H04B 5/02 455/41.1 |
| 2016/0067497 A1* | 3/2016 | Levine | A61B 5/4836 607/62 |
| 2016/0072303 A1* | 3/2016 | Jeong | H04B 5/0037 307/104 |
| 2016/0079773 A1* | 3/2016 | Shinoda | H02J 50/502 320/108 |
| 2016/0087689 A1* | 3/2016 | Fukaya | H02J 50/10 307/104 |
| 2016/0157769 A1* | 6/2016 | Min | A61B 5/4887 600/547 |
| 2017/0181087 A1* | 6/2017 | Kato | H04W 4/80 |
| 2017/0272128 A1* | 9/2017 | Tanaka | H04B 5/0081 |
| 2018/0048055 A1* | 2/2018 | O'Driscoll | H01Q 7/00 |
| 2018/0140852 A1 | 5/2018 | Linder et al. | |
| 2018/0207429 A1* | 7/2018 | Reinke | A61B 5/6867 |
| 2018/0212583 A1* | 7/2018 | Toujo | H03H 7/075 |
| 2019/0143128 A1* | 5/2019 | Weijand | A61N 1/37223 340/539.12 |
| 2019/0167989 A1* | 6/2019 | Guyon | A61N 1/3787 |
| 2019/0175902 A1* | 6/2019 | Lee | G06F 3/015 |
| 2020/0014216 A1* | 1/2020 | Hwang | H02J 50/80 |
| 2020/0064920 A1* | 2/2020 | Soltani | A61N 1/37223 |
| 2020/0108252 A1* | 4/2020 | Zellmer | A61F 2/482 |
| 2020/0274394 A1* | 8/2020 | Rhee | H02J 7/0029 |
| 2020/0393932 A1 | 12/2020 | Kida et al. | |
| 2021/0012945 A1 | 1/2021 | Ridler et al. | |
| 2021/0083370 A1* | 3/2021 | Landherr | H01Q 7/00 |
| 2021/0145362 A1* | 5/2021 | Hosotani | H02J 50/10 |
| 2021/0159731 A1* | 5/2021 | Nakao | H04B 5/0037 |
| 2021/0320527 A1* | 10/2021 | Lee | H04B 5/0081 |
| 2022/0045619 A1* | 2/2022 | Jia | H02M 7/5387 |
| 2022/0133183 A1* | 5/2022 | Garai | A61B 5/6833 600/365 |
| 2023/0198523 A1* | 6/2023 | Sun | H03K 17/955 200/600 |
| 2023/0253475 A1* | 8/2023 | Gosavi | H03H 9/17 257/295 |

OTHER PUBLICATIONS

Extended European search report issued on Jul. 25, 2022, in counterpart European Patent Application No. 21211325.2 (12 pages in English).

* cited by examiner

METHOD AND APPARATUS WITH WIRELESS POWER RECEPTION, WIRELESS COMMUNICATION, AND ELECTRICAL STIMULATION

CROSS-REFERENCE TO RELATED APPLICATIONS

This application claims the benefit under 35 USC § 119(a) of Korean Patent Application No. 10-2021-0041908, filed on Mar. 31, 2021, in the Korean Intellectual Property Office, the entire disclosure of which is incorporated herein by reference for all purposes.

BACKGROUND

1. Field

The following description relates to a method and apparatus with wireless power reception, wireless communication, and electrical stimulation.

2. Description of Related Art

An implantable device may be inserted into a human body and used for sensing biometric information or for treatment. Since the implantable device is inserted into a human body, the implantable device may have a small volume. Since it may be difficult to attach or detach the implantable device, power may be wirelessly supplied from outside a human body instead of replacing a battery of the implantable device. To wirelessly supply power to the implantable device inserted into the human body and simultaneously apply a stimulation signal to the human body, a wireless power receiver may use an electrode for electrical stimulation and a coil for wirelessly receiving power.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, an electronic apparatus includes: an external coil connected via a pair of a first feed-through portion and a second feed-through portion to a communication circuit, the external coil comprising a first coil part and a second coil part disposed outside a housing; a wireless power transmission circuit; an electrode signal processing circuit included in the housing; an external capacitor disposed outside the housing and connected between the first coil part and the second coil part; a first electrode connected to the first coil part at one end of the external capacitor; and a second electrode connected to the second coil part at another end of the external capacitor.

The first coil part may be connected in series between the one end of the external capacitor and the first feed-through portion, the second coil part may be connected in series between the other end of the external capacitor and the second feed-through portion, and the first coil part and second coil may have equivalent impedance.

The electrode signal processing circuit may be connected to the first coil part via an inductor, may be connected to the second coil part via another inductor, and may be configured to perform either one or both of applying of an electrode signal to the first electrode and the second electrode and sensing of an electrode signal from the first electrode and the second electrode.

The inductors connected to the electrode signal processing circuit may be configured to pass an electrode signal of a first frequency band and to block an electrode signal of the other frequency bands higher than the first frequency band, between the external coil and the electrode signal processing circuit.

The wireless power transmission circuit may be connected to the first coil part via an inductor and a capacitor that are connected in series to each other, may be connected to the second coil part via another inductor and another capacitor that are connected in series to each other, and may be configured to wirelessly receive power from an external device via the external coil.

A combination of the inductor and the capacitor that are connected in series to each other, and a combination of the other inductor and the other capacitor that are connected in series to each other may receive power of a second frequency band between a first frequency band and a third frequency band and block an electrode signal of the first frequency band and a communication signal of the third frequency band, between the external coil and the wireless power transmission circuit.

The communication circuit may be connected to the first coil part via a capacitor, may be connected to the second coil part via another capacitor, and may be configured to communicate with an external device using any one or any combination of the external coil, the first electrode, and the second electrode.

The capacitors connected to the communication circuit may be configured to block an electrode signal of a first frequency band and power of a second frequency band higher than the first frequency band and to pass a communication signal of a third frequency band higher than the second frequency band, between the external coil and the communication circuit.

The first electrode and the second electrode may be disposed on different sides of the external capacitor disposed outside the housing.

The first electrode and the second electrode may be spaced apart from each other by 2 centimeters (cm) or greater.

An area of an overlapping region between a plane region occupied by the external coil and a region occupied by the housing in a plane on which the external coil is disposed may be less than or equal to a threshold area.

The first electrode and the second electrode may be disposed on a same side based on the housing and may be configured to provide electrode signals to beta cells disposed between the first electrode and the second electrode.

In another general aspect, an electronic apparatus includes: an external element that is either one or both of an external coil and an external electrode disposed outside a housing; a communication circuit connected to the external element in series via a capacitor and configured to operate the external element as either one of a monopole antenna and a dipole antenna in a communication frequency band; and an additional circuit connected to the external element in series via an inductor.

The apparatus may include: a first internal capacitor connected between both ends of the external coil, wherein the additional circuit may include a wireless power transmission circuit connected to the external coil in series via an inductor.

The external electrode may include a pair of a first electrode and a second electrode, and the additional circuit may include an electrode signal processing circuit connected to the first electrode in series via an inductor and connected to the second electrode in series via another inductor.

The apparatus may include: a second internal capacitor connected between the first electrode and the second electrode.

The first electrode may be connected to the communication circuit in series via a capacitor, and the second electrode may be connected to the communication circuit in series via another capacitor.

The first electrode may be connected to the communication circuit in series via a capacitor and connected to the electrode signal processing circuit via an inductor, and the second electrode may be connected to a ground via another capacitor and connected to the electrode signal processing circuit.

The external element may include both the external coil and the external electrode, and the communication circuit may be connected to both the external coil and the external electrode, and may be configured to select an external element that exhibits relatively high communication performance among communication performance using the external coil and communication performance using the external electrode, and to perform a communication.

The external element further may include an external antenna connected to the communication circuit, and the communication circuit may be connected to the external coil, the external electrode and the external antenna, and may be configured to select an external element that exhibits highest communication performance among communication performance using the external coil, communication performance using the external electrode and communication performance using the external antenna, and to perform a communication.

The external coil may be connected via a pair of a first feed-through portion and a second feed-through portion to the communication circuit and the additional circuit, and the external coil may include a first coil part and a second coil part disposed outside the housing, and the apparatus further may include an external capacitor disposed outside the housing and connected between the first coil part and the second coil part, and the external capacitor may include a first electrode connected to the first coil part at one end of the external capacitor, and a second electrode connected to the second coil part at another end of the external capacitor.

In another general aspect, an electronic apparatus includes: an external element including either one of an external coil and an external electrode; a capacitor configured to control transmission of an electrical signal between the external element and a communication circuit based on a frequency band of the electrical signal; and an inductor configured to control transmission of the electrical signal between the external element and an additional circuit based on the frequency band.

The capacitor may be configured to: pass the electrode signal between the external element and the communication circuit, in response to the frequency band being a higher frequency band; and block the electrode signal between the external element and the communication circuit, in response to the frequency band being a lower frequency band.

The inductor may be configured to: pass the electrode signal between the external element and the additional circuit, in response to the frequency band being a lower frequency band; and block the electrode signal between the external element and the additional circuit, in response to the frequency band being a higher frequency band.

The additional circuit may include either one of: a wireless power transmission circuit connected to the external coil; and an electrode signal processing circuit connected to the external electrode.

Other features and aspects will be apparent from the following detailed description, the drawings, and the claims.

Figure 1:
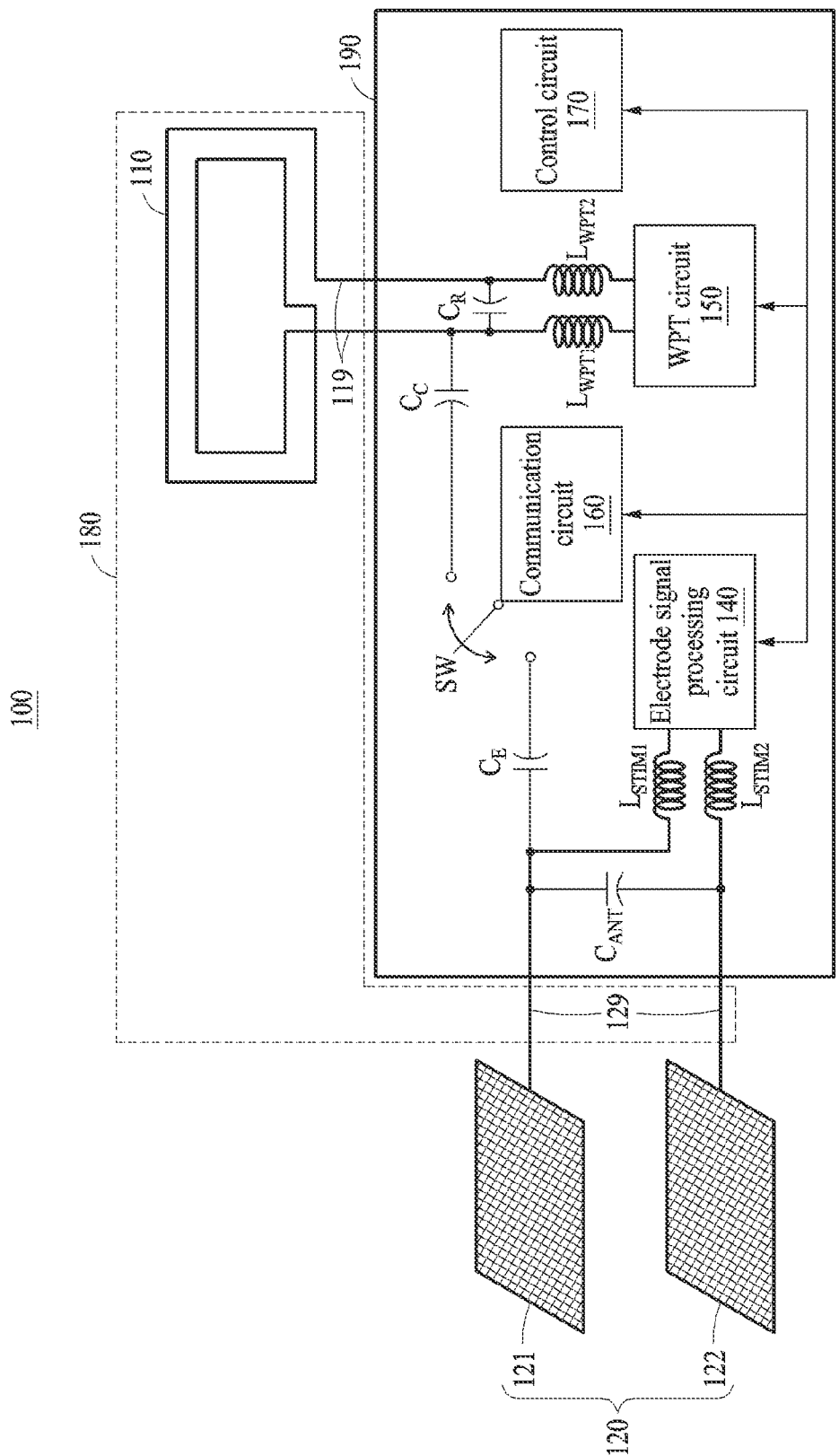
FIG. 1 illustrates an example of a configuration of an electronic apparatus.

Throughout the drawings and the detailed description, unless otherwise described or provided, the same drawing reference numerals will be understood to refer to the same elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known, after an understanding of the disclosure of this application, may be omitted for increased clarity and conciseness.

The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

The following structural or functional descriptions of examples disclosed in the present disclosure are merely intended for the purpose of describing the examples and the examples may be implemented in various forms. The examples are not meant to be limited, but it is intended that various modifications, equivalents, and alternatives are also covered within the scope of the claims.

Although terms of "first" or "second" are used herein to describe various components, members, regions, layers, or sections, the components, members, regions, layers, or sections, are not limited to the terms. Rather, these terms should be used only to distinguish one component, member, region, layer, or section, from another component, member, region, layer, or section. For example, a "first" component, member, region, layer, or section may be referred to as a "second" component, member, region, layer, or section, or similarly, and the "second" component may be referred to as the "first" component within the scope of the right according to the concept of the present disclosure.

Throughout the specification, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween. Likewise, expressions, for example, "between" and "immediately between" and "adjacent to" and "immediately adjacent to" may also be construed as described in the foregoing.

The terminology used herein is for the purpose of describing particular examples only and is not to be limiting of the examples. As used herein, the singular forms "a," "an," and "the" are intended to include the plural forms as well, unless the context clearly indicates otherwise. As used herein, the term "and/or" includes any one and any combination of any two or more of the associated listed items. As used herein, the terms "include," "comprise," and "have" specify the presence of stated features, numbers, operations, elements, components, and/or combinations thereof, but do not preclude the presence or addition of one or more other features, numbers, operations, elements, components, and/or combinations thereof. The use of the term "may" herein with respect to an example or embodiment (for example, as to what an example or embodiment may include or implement) means that at least one example or embodiment exists where such a feature is included or implemented, while all examples are not limited thereto.

Unless otherwise defined, all terms used herein including technical or scientific terms have the same meanings as those generally understood consistent with and after an understanding of the present disclosure. Terms, such as those defined in commonly used dictionaries, should be construed to have meanings matching with contextual meanings in the relevant art and the present disclosure, and are not to be construed as an ideal or excessively formal meaning unless otherwise defined herein.

Hereinafter, examples will be described in detail with reference to the accompanying drawings, and like reference numerals in the drawings refer to like elements throughout.

FIG. 1 illustrates an example of a configuration of an electronic apparatus.

In an example, an electronic apparatus 100 may perform an electrical stimulation, a wireless power reception, and a wireless communication. The electronic apparatus 100 may include an external element, a communication circuit 160, and an additional circuit. The external element may be an element disposed outside a housing 190, and may include at least one of an external coil 110 and an external electrode. The external electrode may be an electrode pair 120 including a first electrode 121 and a second electrode 122. The additional circuit may be a circuit for functions (for example, the electrical stimulation and the wireless power reception) other than the wireless communication, and may include, for example, an electrode signal processing circuit 140 and/or a wireless power transmission circuit (hereinafter, referred to as a "WPT circuit") 150. The electronic apparatus 100 may also include a control circuit 170.

The communication circuit 160 may be connected in series to the above-described external element via a capacitor. For example, the electronic apparatus 100 may include a plurality of external elements (e.g., the external coil 110 and the electrode pair 120), and the external coil 110 may be connected in series to the communication circuit 160 via a capacitor $C_c$ at a first end of the external coil 110. The electrode pair 120 may be connected in series to the communication circuit 160 via a capacitor $C_E$. The communication circuit 160 may be selectively connected to one of the plurality of external elements by a switch SW. For example, the communication circuit 160 may be connected to the electrode pair 120 or the external coil 110 by the switch SW.

Also, the communication circuit 160 may operate at least one external element as one of a monopole antenna and a dipole antenna in a communication frequency band. For example, when the electronic apparatus 100 includes a plurality of external elements, an element connected to the communication circuit 160 among the plurality of external elements may operate as one of a monopole antenna and a dipole antenna.

The additional circuit may be connected in series to the above-described external element via an inductor. In an example, the electrode signal processing circuit 140 may be connected in series to the electrode pair 120 via inductors $L_{STIM1}$ and $L_{STIM2}$. The first electrode 121 may be connected in series via the inductor $L_{STIM1}$ to the electrode signal processing circuit 140, and the second electrode 122 may be connected in series via the inductor $L_{STIM2}$ to the electrode signal processing circuit 140. In another example, the WPT circuit 150 may be connected in series to the external coil 110 via inductors $L_{WPT1}$ and $L_{WPT2}$. A first end of the external coil 110 may be connected in series via the inductor $L_{WPT1}$ to the WPT circuit 150 and a second end of the external coil 110 may be connected in series via the inductor $L_{WPT2}$ to the WPT circuit 150.

The control circuit 170 may control operations of the electrode signal processing circuit 140, the WPT circuit 150, and the communication circuit 160 that are described above. Also, the control circuit 170 may connect the communication circuit 160 to the external coil 110 or the electrode pair 120 via the switch SW. For example, the control circuit 170 may manage a distribution of power received from the WPT circuit 150 and a charging of a battery. The control circuit 170 may transmit biometric sensing information and receive a stimulation parameter via the wireless communication circuit 160. The control circuit 170 may operate the electrode signal processing circuit 140 based on the stimulation parameter to apply voltage and/or current according to the stimulation parameter to an electrode. The control circuit 170 may sense voltage and current applied to the electrode through the electrode signal processing circuit 140.

The electrode signal processing circuit 140 may apply an electrical stimulation to an object (for example, a human body, body tissues, and/or body substances) using the external electrode that is an external element, or may sense biometric information from the object. The electrode signal processing circuit 140 may apply or sense an electric signal of a first frequency band. For example, the electronic apparatus 100 may perform an electrical stimulation and/or sense biometric information using the electrode pair 120 in a first frequency band (for example, an electrical stimulation frequency band). A second internal capacitor $C_{ANT}$ may be open in the first frequency band, and the electronic apparatus 100 may form an electric field (E-field) between the first electrode 121 and the second electrode 122 of the electrode pair 120, to apply an electrical stimulation to an object located in a space between the first electrode 121 and the second electrode 122, which will be described below. The object to which the electrical stimulation is to be applied may include, for example, a body tissue, a brain, or beta cells. Also, the electronic apparatus 100 may sense a biometric signal through the electrode pair 120. A non-limiting example of an electrical stimulation and/or sensing of biometric information using the electrode pair 120 will be further described below with reference to FIG. 7. The electrode signal processing circuit 140 may perform one of an electrical stimulation and/or sensing of a biometric signal using the electrode pair 120. To perform both the electrical stimulation and the sensing of the biometric signal, the electrode signal processing circuit 140 may be connected to the electrode pair 120 for one of the electrical stimulation and the sensing of the biometric signal and may be further connected to an additional electrode pair for the other. For example, an electrode for an electrical stimulation may be referred to as a "stimulation electrode", and an electrode for sensing biometric information may be referred to as a "sensing electrode".

The WPT circuit 150 may wirelessly receive power from an external device using the external coil 110 that is an external element. The WPT circuit 150 may receive power wirelessly transmitted in a second frequency band. For example, the electronic apparatus 100 may wirelessly receive power from the external device via the external coil 110 in the second frequency band (for example, a wireless power transmission frequency band). A non-limiting example of a wireless power reception via the external coil 110 will be further described below with reference to FIG. 3. In the present specification, an example in which the WPT circuit 150 performs an operation of wirelessly receiving power from an external device (for example, a smartphone) will be mainly described. However, an operation of the WPT circuit 150 is not limited thereto, and the WPT circuit 150 may also wirelessly transmit power to an external device, depending on a design.

The communication circuit 160 may establish a wireless communication with an external device in a third frequency band using the external element. For example, the electronic apparatus 100 may operate the external coil 110 and/or the external electrode as an antenna in the third frequency band (for example, a communication frequency band) to establish the wireless communication with the external device. The electronic apparatus 100 may operate the external element (for example, the external coil 110 or the electrode pair 120) that is connected to the communication circuit 160 by the switch SW as an antenna. A first internal capacitor $C_R$ and a second internal capacitor $C_{ANT}$ may be shorted in the third frequency band, so that the external coil 110 and the electrode pair 120 may operate as antennas, a non-limiting example of which will be further described below. For example, the electronic apparatus 100 may include both an external coil and an external electrode, and the communication circuit 160 may be connected to both the external coil and the external electrode, may select an external element that exhibits greater communication performance among communication performance using the external coil and communication performance using the external electrode by the control circuit 170, and may perform a communication using the selected external element. The communication performance may be, for example, a measure indicating a capability of performing a communication using a selected external element, and may be an index, for example, a magnitude of a received signal, or a signal-to-noise ratio (SNR). However, examples are not limited thereto, and in another example the electronic apparatus 100 may simultaneously operate both the external coil 110 and the electrode pair 120 as antennas without the switch SW.

In other words, the electronic apparatus 100 may perform a wireless power reception and a wireless communication for each frequency band using the external coil 110, and may perform an electrical stimulation and a wireless communication using the electrode pair 120. For example, the first frequency band may include a frequency band of 0 hertz (Hz) to 1 kilohertz (KHz), inclusive, the second frequency band may include a frequency band of 0.1 megahertz (MHz) to 20 MHz, inclusive, and the third frequency band may include a frequency band of 400 MHz to 10 gigahertz (GHz), inclusive.

The housing 190 may accommodate the electrode signal processing circuit 140, the WPT circuit 150, the communication circuit 160, and the control circuit 170. The housing 190 may be formed of, for example, a metal material such as titanium. The electronic apparatus 100 may include a molding 180 to seal a feed-through portion in the housing 190. For example, the molding 180 may accommodate the external coil 110, a conducting line portion 119 of the external coil 110 passing through the feed-through portion of the housing 190, and a conducting line portion 129 of the electrode pair 120 passing through the feed-through portion of the housing 190. The molding 180 may block an inflow of liquid (for example, body fluid) into the external coil 110 and the conducting line portions 119 and 129 and/or an access to the external coil 110 and the conducting line portions 119 and 129. Also, one surface of the first electrode 121 and one surface of the second electrode 122 in the electrode pair 120 may be exposed to be in contact with the liquid, whereas another surface of the first electrode 121 and another surface of the second electrode 122 may be covered by the molding 180. However, examples are not limited thereto, and in another example both the surfaces of each of the first electrode 121 and the second electrode 122 in the electrode pair 120 may also be exposed to be in contact with the liquid.

In an example, the electronic apparatus 100 may be accommodated in a small-sized housing and may be inserted into a human body. The electronic apparatus 100 may perform a treatment operation through an electrical stimulation for an object. Also, the electronic apparatus 100 may sense biometric information from the external electrode. For example, a surface of the external electrode in contact with external liquid (for example, body fluid) may be coated with an enzyme that reacts with blood sugar, and an electric signal may be generated due to a reaction between blood sugar and the enzyme in a human body in the external electrode. The electronic apparatus 100 may sense the electric signal as biometric information. However, the biometric information is not limited thereto and may include all information associated with a living body that may be sensed through an electrode, for example, an electroencephalogram (EEG) signal, a bioelectric signal, an electrocardiogram (ECG) signal, impedance of a body tissue, or voltage and current applied to a sensing electrode. The electronic apparatus 100 may establish a wireless communication with an external device outside a human body (for example, a smart device such as a smartphone and/or a tablet), to transfer sensed biometric information or receive parameters (for example, a magnitude of voltage, a magnitude of current, or a frequency of an electrical stimulation) for biometric stimulation from the external device. Also, the electronic apparatus 100 may wirelessly receive power from the external device via the external coil 110.

The external coil 110 or the external electrode may each be used for two functions even though a separate antenna is absent, and accordingly a form factor or size of the electronic apparatus 100 for wireless communication may be advantageously minimized. Also, an external element that radiates radio waves for a communication with the external device may be disposed outside the housing 190, and thus the electronic apparatus 100 may have enhanced radiation performance even in the minimized form factor. Due to an increase in the radiation performance, power consumption may also be advantageously reduced. The electronic apparatus 100 may perform a communication in the third frequency band, to have a transmission and reception distance greater than or equal to 1 meter (m). The electronic apparatus 100 may control the switch SW, to select an external element that exhibits optimal reception performance and to operate the external element as an antenna.

Non-limiting examples in which the communication circuit 160 and the external coil 110 are connected will be further described below with reference to FIGS. 2 to 4. Non-limiting examples in which the communication circuit 160 and the electrode pair 120 are connected will be further described below with reference to FIGS. 6 to 8. However, a circuit of the electronic apparatus 100 is not limited to that of FIG. 1. The electronic apparatus 100 may also be implemented as a circuit that includes either the external coil 110 or the electrode pair 120 as an external element without the switch SW. A circuit with only the external coil 110 may correspond to circuits of FIGS. 2 to 4, and a circuit with only the external electrode may correspond to circuits of FIGS. 6 to 8, according to non-limiting examples.

FIGS. 2 to 5 illustrate examples of a hardware implementation of an electronic apparatus that performs a wireless power reception and a wireless communication using a coil.

Figure 2:
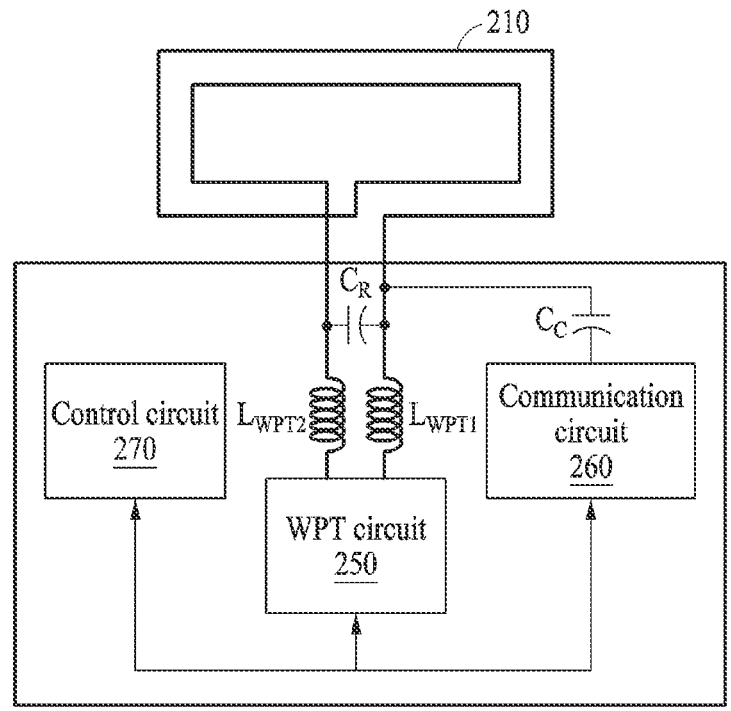
FIGS. 2 to 5 illustrate examples of a hardware implementation of an electronic apparatus that performs a wireless power transmission and a wireless communication using a coil.

FIG. 2 illustrates an example of a structure in which an external coil 210 is connected to a communication circuit 260. An electronic apparatus may include a WPT circuit 250 as an additional circuit. The WPT circuit 250 may be connected in series via inductors $L_{WPT1}$ and $L_{WPT2}$ to the external coil 210 at both ends of the external coil 210. The electronic apparatus may include a first internal capacitor $C_R$ connected between the ends of the external coil 210. In other words, the ends of the external coil 210 may be connected in parallel by the first internal capacitor $C_R$. A resonant frequency may be determined by capacitance of the first internal capacitor $C_R$ and inductance of the external coil 210. The resonant frequency may belong to a second frequency band. One end of the external coil 210 may be connected in series via a capacitor $C_c$ to the communication circuit 260.

A control circuit 270 may control the WPT circuit 250 and the communication circuit 260.

Figure 3:
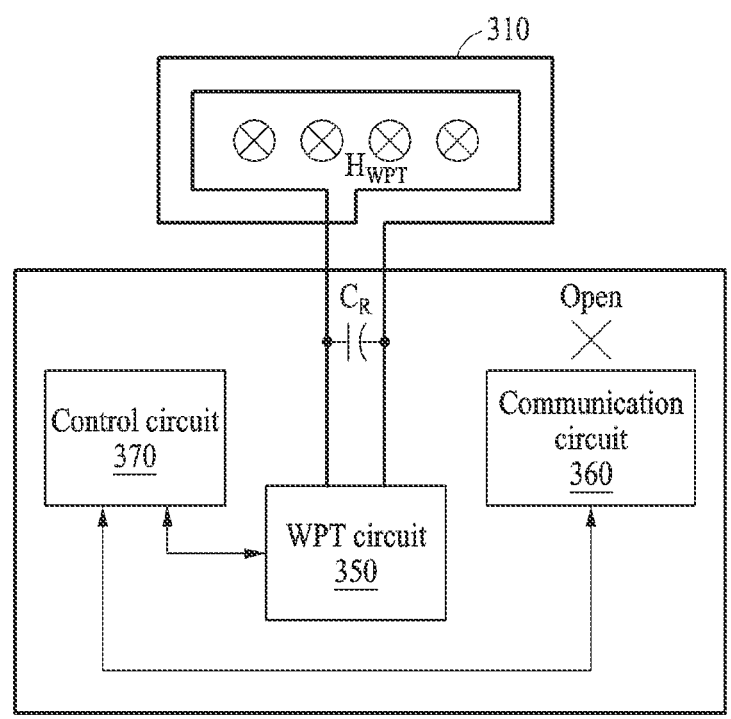

FIG. 3 illustrates an operation of a circuit of FIG. 2 in the second frequency band. The second frequency band may be, for example, in a range of 0.1 MHz to 20 MHz, inclusive.

The capacitor $C_c$ may have capacitance within a first capacitance range in which both ends of the capacitor $C_c$ are open in a first frequency band and the second frequency band and are shorted in a third frequency band. The capacitance of the capacitor $C_c$ may have a value between 10 picofarads (pF) and 100 pF, inclusive. For example, the ends of the capacitor $C_c$ may be electrically disconnected in the first frequency band and the second frequency band. As shown in FIG. 3, the capacitor $C_c$ may disconnect an external coil 310 from a communication circuit 360 when the circuit is in the second frequency band.

Also, inductors $L_{WPT1}$ and $L_{WPT2}$ may have inductance within a first inductance range in which both ends of each of the inductors $L_{WPT1}$ and $L_{WPT2}$ are shorted in the first frequency band and the second frequency band and are open in the third frequency band. The inductance of the inductors $L_{WPT1}$ and $L_{WPT2}$ may have, for example, a value between 10 nanohenry (nH) and 100 nH, inclusive. For example, the ends of the inductors $L_{WPT1}$ and $L_{WPT2}$ may be electrically connected in the first frequency band and the second frequency band, and the inductors $L_{WPT1}$ and $L_{WPT2}$ may connect the external coil 310 and a WPT circuit 350 when the circuit is in the second frequency band, as shown in FIG. 3.

The WPT circuit 350 may perform a wireless power reception at a resonant frequency determined based on inductance of the external coil 310 and capacitance of the first internal capacitor $C_R$. The WPT circuit 350 may wirelessly receive power through the external coil 310 based on a control of the control circuit 370. The external coil 310 may wirelessly receive power based on a magnetic field $H_{WPT}$ in a direction perpendicular to a plane of the external coil 310. The wireless power reception may be performed by, for example, a magnetic induction scheme, a magnetic resonance scheme, and/or an electromagnetic wave scheme.

Figure 4:
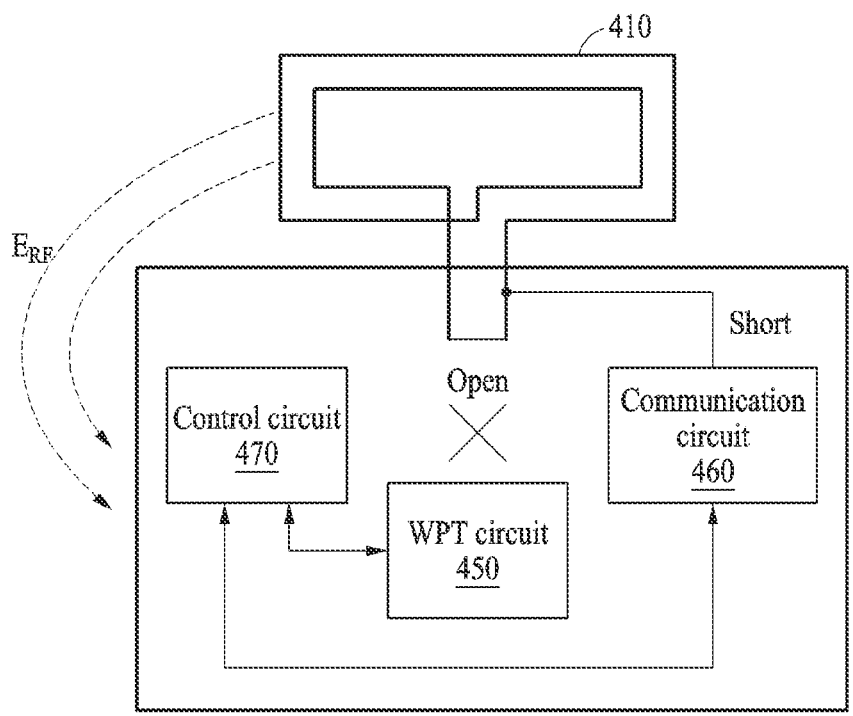

FIG. 4 illustrates an operation of the circuit of FIG. 2 in the third frequency band. The third frequency band may be, for example, in a range of 400 MHz to 10 GHz, inclusive. The first internal capacitor $C_R$ may have capacitance within a second capacitance range in which both ends of the first internal capacitor $C_R$ are open in the first frequency band and are shorted in the third frequency band. The capacitance of the first internal capacitor $C_R$ may have, for example, a value between 0.1 nanofarads (nF) and 10 pF, inclusive. As shown in FIG. 4, the ends of the first internal capacitor $C_R$ may be electrically shorted in the third frequency band so that both ends of an external coil 410 may be connected. Thus, the external coil 410 may operate as an integrated metal antenna (for example, a monopole antenna).

Also, the ends of each of the inductors $L_{WPT1}$ and $L_{WPT2}$ may be open in the third frequency band, as described above. The inductors $L_{WPT1}$ and $L_{WPT2}$ may electrically disconnect the external coil 410 from a WPT circuit 450.

A communication circuit 460 may radiate a radio wave for a wireless communication through the external coil 410, or may receive a radio wave from an external device. An electric field $E_{RF}$ from the external coil 410 towards a housing formed of metal may be formed. The WPT circuit 450 may be disconnected from the external coil 410, and accordingly the WPT circuit 450 may be excluded from a wireless communication operation. A control circuit 470 may operate the communication circuit 460 in the third frequency band and may stop an operation of the WPT circuit 450.

Figure 5:
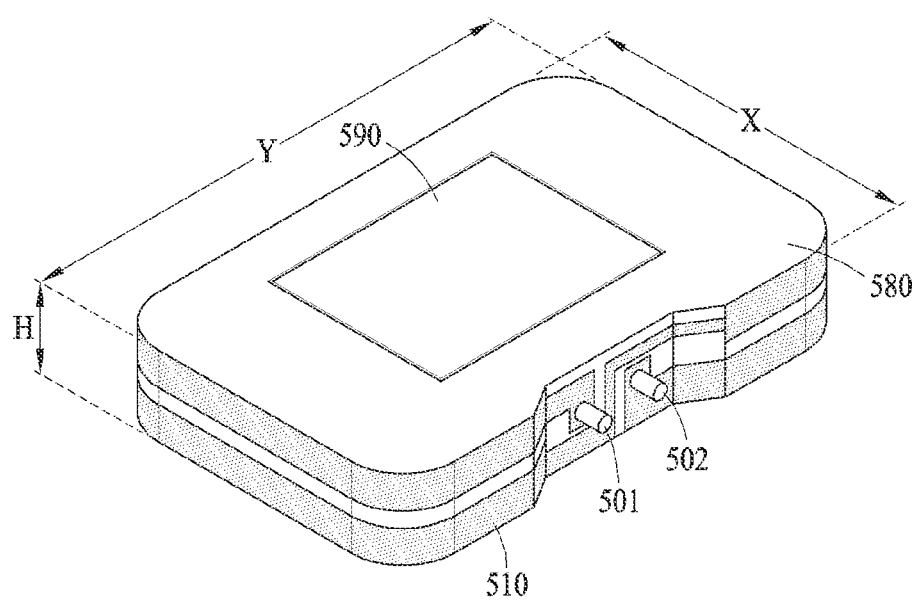

FIG. 5 illustrates an example in which the circuits described above with reference to FIGS. 2 to 4 are accommodated in a housing 590 and a molding 580. For example, an electronic apparatus may be implemented in a form factor of a width X of 18.4 millimeters (mm), a length Y of 23.2 mm, and a height H of 4 mm, and an external coil 510 may have a size of 22 mm×17 mm×3 mm. When a signal is emitted to the electronic apparatus inserted into a medium (for example, a living body) by a depth of 3 centimeters (cm) at transmitted power of 0 decibel-milliwatts (dBm), an average gain of signals received by the electronic apparatus may be −35 decibels (dB). "Received power=transmitted power+antenna gain−spatial radiation loss" may be represented as "−75 dBm=0 dBm−35 dB−40 dB". In other words, power consumption of the inductors $L_{WPT1}$ and $L_{WPT2}$, the first internal capacitor $C_R$, and the capacitor $C_c$ that are described above may be less than or equal to 1% of received power. Thus, the electronic apparatus may be advantageously implemented in a miniaturized form factor while minimizing a reduction in the received power. In addition, when the above-described external coil 510 operates as a monopole antenna, the electronic apparatus may have a transmission and reception distance greater than or equal to 1 meter (m) at 2.45 GHz in the third frequency band. As shown in FIG. 5, the external coil 510 may be connected to circuits included in the housing 590 via a pair of feed-through portions (for example, a first feed-through port 501 and a second feed-through port 502).

In the above example, a form factor for insertion into a human body is described. For a relatively small animal, the electronic apparatus may be implemented with a size of 12 mm×12 mm×4 mm. In this example, the electronic apparatus may be miniatured while minimizing a decrease in performance.

Figure 6:
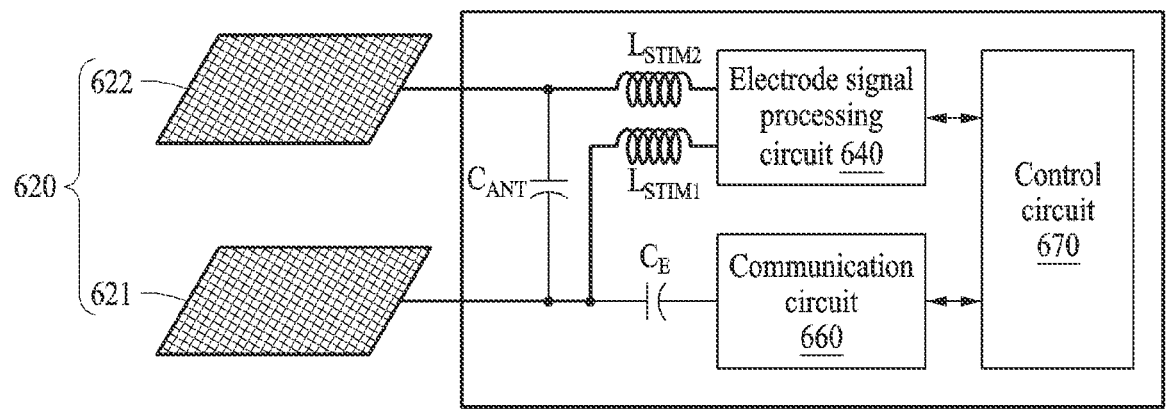
FIGS. 6 to 8 illustrate examples of a hardware implementation of an electronic apparatus that performs an electrical stimulation and a wireless communication using an electrode.
Figure 7:
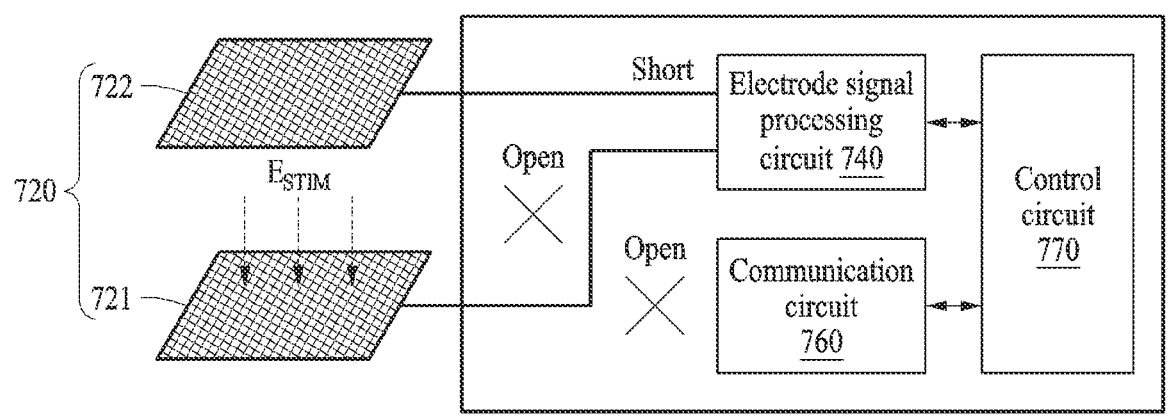
Figure 8:
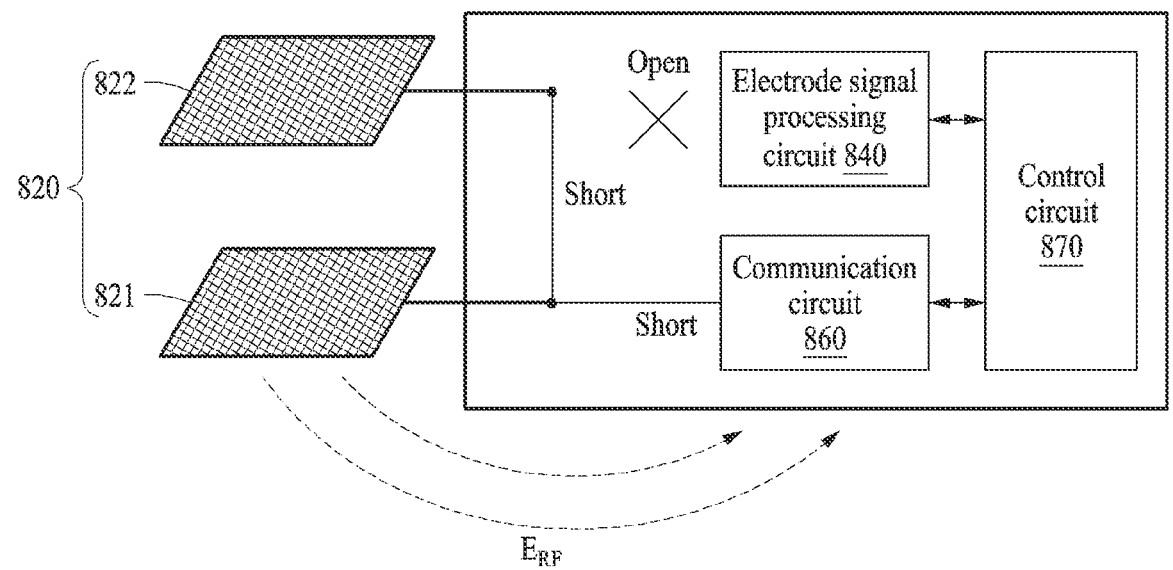

FIGS. 6 to 8 illustrate examples of a hardware implementation of an electronic apparatus that performs an electrical stimulation and a wireless communication using an electrode.

FIG. 6 illustrates an example of a structure in which an external electrode is connected to an electrode signal processing circuit 640. The external electrode may include an electrode pair 620 including a first electrode 621 and a second electrode 622, and an electronic apparatus may include the electrode signal processing circuit 640 as an additional circuit. The electrode signal processing circuit 640 may be connected to the first electrode 621 in series via an inductor $L_{STIM1}$, and may be connected to the second electrode 622 in series via an inductor $L_{STIM2}$. The electronic apparatus may further include a second internal capacitor $C_{ANT}$ connected between the first electrode 621 and the second electrode 622. In other words, the second internal capacitor $C_{ANT}$ may be connected in parallel to the first electrode 621 and the second electrode 622. The first electrode 621 may be connected in series via a capacitor $C_E$ to a communication circuit 660. A control circuit 670 may control the electrode signal processing circuit 640 and the communication circuit 660.

FIG. 7 illustrates an operation of a circuit of FIG. 6 in a first frequency band. The first frequency band may be, for example, in a range of 0 Hz to 1 kHz, inclusive.

The inductors $L_{STIM1}$ and $L_{STIM2}$ may have inductance within a second inductance range in which both ends of the inductors $L_{STIM1}$ and $L_{STIM2}$ are shorted in the first frequency band and are open in a second frequency band and a third frequency band. The inductance of the inductors $L_{STIM1}$ and $L_{STIM2}$ may have, for example, a value between 0.1 microhenry (μH) and 10 μH, inclusive, and may be 1 μH.

Also, the second internal capacitor $C_{ANT}$ may have capacitance within a second capacitance range in which both ends of the second internal capacitor $C_{ANT}$ are open in the first frequency band and are shorted in the third frequency band. The capacitance of the second internal capacitor $C_{ANT}$ may have, for example, a value between 0.1 nF and 10 nF, inclusive. The capacitor $C_E$ may have capacitance within a first capacitance range in which both ends of the capacitor $C_E$ are open in the first frequency band and the second frequency band and are shorted in the third frequency band. The capacitance of the capacitor $C_E$ may have, for example, a value between 10 pF and 100 pF, inclusive.

As shown in FIG. 7, the ends of the capacitor $C_E$ may be open in the first frequency band, and accordingly a communication circuit 760 may be disconnected from an electrode pair 720 including a first electrode 721 and a second electrode 722. The ends of the inductors $L_{STIM1}$ and $L_{STIM2}$ may be shorted in the first frequency band, and accordingly each of the first electrode 721 and the second electrode 722 of the electrode pair 720 may be connected to an electrode signal processing circuit 740. Also, the ends of the second internal capacitor $C_{ANT}$ may be open in the first frequency band, and accordingly the first electrode 721 and the second electrode 722 may be separated from each other and may be individually connected to the electrode signal processing circuit 740.

The electrode signal processing circuit 740 may apply an electric field $E_{STIM}$ to a space between the first electrode 721 and the second electrode 722 based on a control of a control circuit 770. However, examples are not limited thereto, and the electrode signal processing circuit 740 may also sense biometric information from an external electrode (for example, at least one of the first electrode 721 and the second electrode 722 of the electrode pair 720).

FIG. 8 illustrates an operation of a circuit of FIG. 6 in the third frequency band. In the third frequency band, both ends of each of the second internal capacitor $C_{ANT}$ and the capacitor $C_E$ may be shorted. Thus, an electrode pair 820 including a first electrode 821 and a second electrode 822 may operate as an integrated metal antenna (for example, a monopole antenna).

Also, the ends of the inductors $L_{STIM1}$ and $L_{STIM2}$ may be open as described above, and accordingly the inductors $L_{STIM1}$ and $L_{STIM2}$ may disconnect an electrode signal processing circuit 840 from the electrode pair 820.

A communication circuit 860 may radiate a radio wave for a wireless communication through an external electrode, or may receive a radio wave from an external device. An electric field $E_{RF}$ from the electrode pair 820 towards a housing formed of metal may be generated. When the electrode signal processing circuit 840 is disconnected from the external electrode, the electrode signal processing circuit 840 may be excluded from a wireless communication operation. A control circuit 870 may operate the communication circuit 860 in the third frequency band and may stop an operation of the electrode signal processing circuit 840.

Thus, an electronic apparatus may be inserted into or attached to a human body, to apply an electrical stimulation to the human body, or to sense biometric information from the human body, and to exchange information associated with an electrical stimulation and/or sensing of biometric information with an external device.

Figure 9:
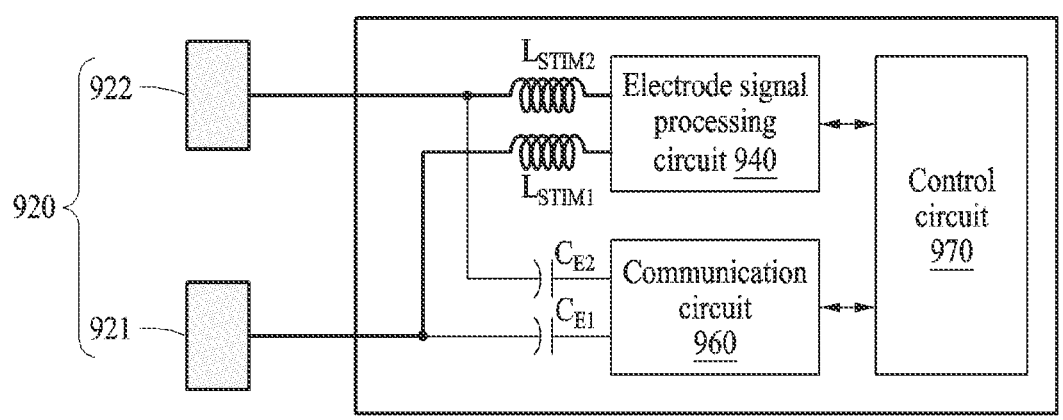
FIGS. 9 to 11 illustrate examples of a hardware implementation of an electronic apparatus that performs an electrical stimulation and a wireless communication based on a dipole structure.
Figure 10:
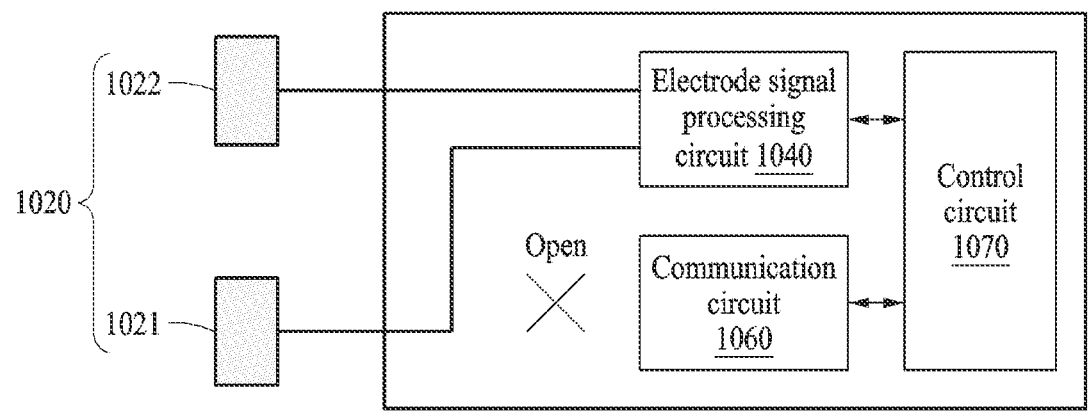
Figure 11:
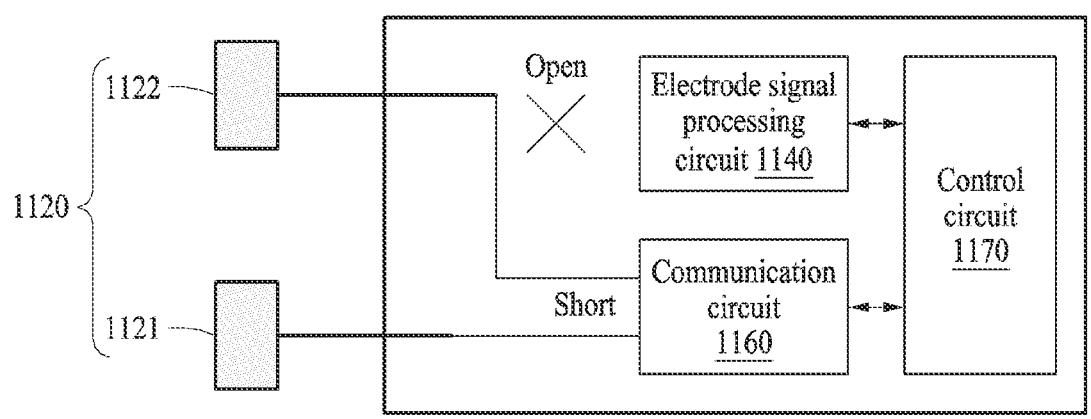

FIGS. 9 to 11 illustrate examples of a hardware implementation of an electronic apparatus that performs an electrical stimulation and a wireless communication based on a dipole structure.

In an example, a first electrode 921 of an electrode pair 920 may be connected in series to a communication circuit 960 via a capacitor $C_{E1}$. A second electrode 922 of the electrode pair 920 may be connected in series to the communication circuit 960 via a capacitor $C_{E2}$. The capacitors $C_{E1}$ and $C_{E2}$ may have capacitance within a first capacitance range in which both ends of each of the capacitors $C_{E1}$ and $C_{E2}$ are open in a first frequency band and a second frequency band and are shorted in a third frequency band, similarly to the above-described capacitor $C_E$. An electrode signal processing circuit 940 may be connected to the electrode pair 920 in series via inductors $L_{STIM1}$ and $L_{STIM2}$. The inductors $L_{STIM1}$ and $L_{STIM2}$ may have inductance within a second inductance range in which both ends of each of the inductors $L_{STIM1}$ and $L_{STIM2}$ are shorted in the first frequency band and are open in the second frequency band and the third frequency band, as described above. A control circuit 970 may control the electrode signal processing circuit 940 and the communication circuit 960.

FIG. 10 illustrates an operation of a circuit of FIG. 9 in the first frequency band. The ends of the inductors $L_{STIM1}$ and $L_{STIM2}$ may be shorted in the first frequency band, and accordingly a first electrode 1021 and a second electrode 1022 of an electrode pair 1020 may be individually connected to an electrode signal processing circuit 1040. The electrode signal processing circuit 1040 may perform an electrical stimulation or sense biometric information based on a control of a control circuit 1070.

The ends of the capacitors $C_{E1}$ and $C_{E2}$ may be open in the first frequency band, and accordingly a communication circuit 1060 may be excluded from an electrical stimulation operation.

FIG. 11 illustrates an operation of the circuit of FIG. 9 in the third frequency band.

The ends of the inductors $L_{STIM1}$ and $L_{STIM2}$ may be open in the third frequency band, and accordingly a first electrode 1121 and a second electrode 1122 of an electrode pair 1120 may be disconnected from an electrode signal processing circuit 1140.

The ends of the capacitors $C_{E1}$ and $C_{E2}$ may be shorted in the third frequency band, and accordingly the electrode pair 1120 may be connected to a communication circuit 1160. The first electrode 1121 and the second electrode 1122 may be electrically separated and may be individually connected to the communication circuit 1160. Thus, the communication circuit 1160 may operate the first electrode 1121 and the second electrode 1122 by applying differential signals to the first electrode 1121 and the second electrode 1122 as a dipole antenna based on a control of a control circuit 1170.

Figure 12:
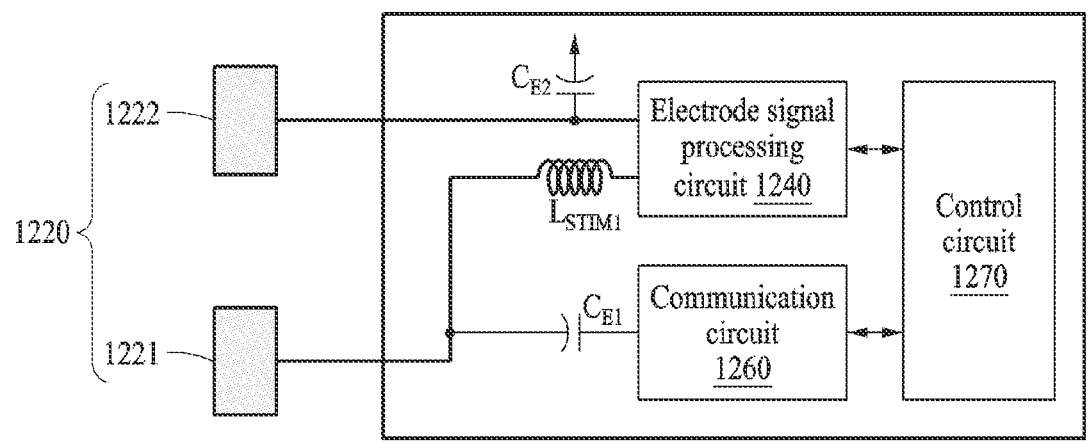
FIGS. 12 to 14 illustrate examples of a hardware implementation of an electronic apparatus that performs an electrical stimulation and a wireless communication based on a monopole structure.
Figure 13:
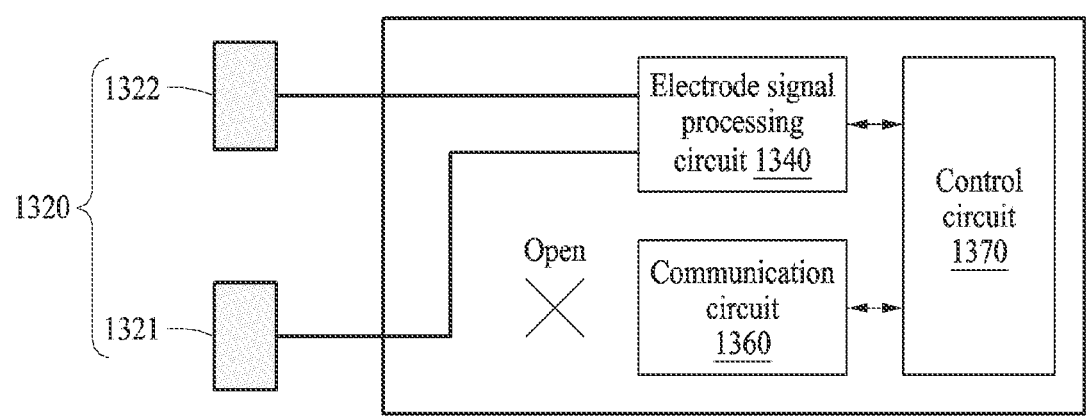
Figure 14:
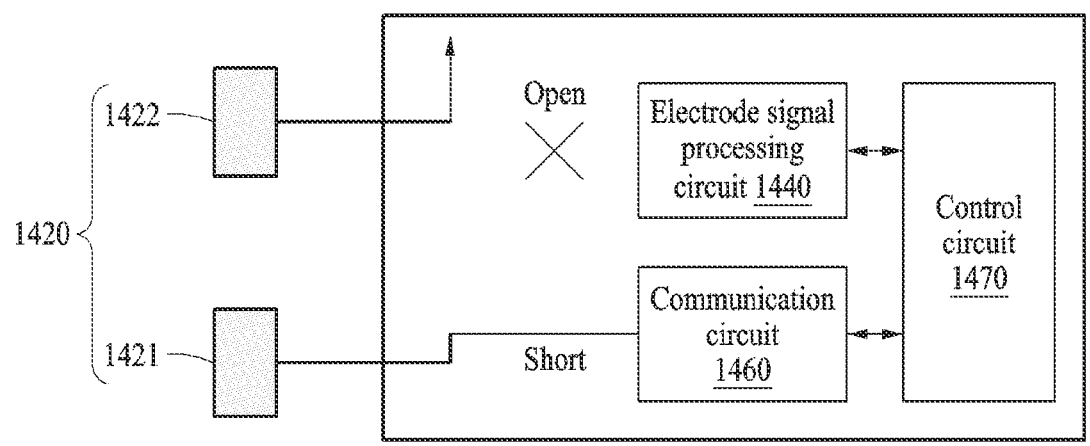

FIGS. 12 to 14 illustrate examples of a hardware implementation of an electronic apparatus that performs an electrical stimulation and a wireless communication based on a monopole structure.

In an example, a first electrode 1221 of an electrode pair 1220 may be connected to a communication circuit 1260 in series via a capacitor $C_{E1}$ and connected to an electrode signal processing circuit 1240 via an inductor $L_{STIM1}$. A second electrode 1222 of the electrode pair 1220 may be connected to the ground via a capacitor $C_{E2}$ and connected to the electrode signal processing circuit 1240. The capacitors $C_{E1}$ and $C_{E2}$ may have capacitance within a first capacitance range in which both ends of each of the capacitors $C_{E1}$ and $C_{E2}$ are open in a first frequency band and a second frequency band and are shorted in a third frequency band, similarly to the above-described capacitor $C_E$. The inductor $L_{STIM1}$ may have inductance within a second inductance range in which both ends of the inductor $L_{STIM1}$ are shorted in the first frequency band and are open in the second frequency band and the third frequency band, as described above. A control circuit 1270 may control the electrode signal processing circuit 1240 and the communication circuit 1260.

FIG. 13 illustrates an operation of a circuit of FIG. 12 in the first frequency band. The ends of the inductor $L_{STIM1}$ may be shorted in the first frequency band, and accordingly a first electrode 1321 and a second electrode 1322 of an electrode pair 1320 may be individually connected to an electrode signal processing circuit 1340. The electrode signal processing circuit 1340 may perform an electrical stimulation or sense biometric information based on a control of a control circuit 1370.

The ends of the capacitors $C_{E1}$ and $C_{E2}$ may be open in the first frequency band, and accordingly a communication circuit 1360 may be excluded from an electrical stimulation operation, and the second electrode 1322 and the ground may be disconnected.

FIG. 14 illustrates an operation of the circuit of FIG. 12 in the third frequency band.

The ends of the inductor $L_{STIM1}$ may be open and the ends of the capacitor $C_{E2}$ may be shorted in the third frequency band, and accordingly a first electrode 1421 and a second electrode 1422 of an electrode pair 1420 may be disconnected from an electrode signal processing circuit 1440.

The ends of the capacitor $C_{E1}$ may be shorted in the third frequency band, and accordingly the first electrode 1421 may be connected to a communication circuit 1460. For example, the second electrode 1422 may be excluded and the first electrode 1421 may be connected to the communication circuit 1460. Thus, the communication circuit 1460 may operate the first electrode 1421 as a monopole antenna by applying a single signal to the first electrode 1421 based on a control of a control circuit 1470.

Mesh electrodes are shown in FIGS. 6 to 8 and plate electrodes are shown in FIGS. 9 to 14, however, a shape of an electrode is not limited thereto. Such shapes of electrodes are merely examples, and any electrode having any shape may be used.

Figure 15:
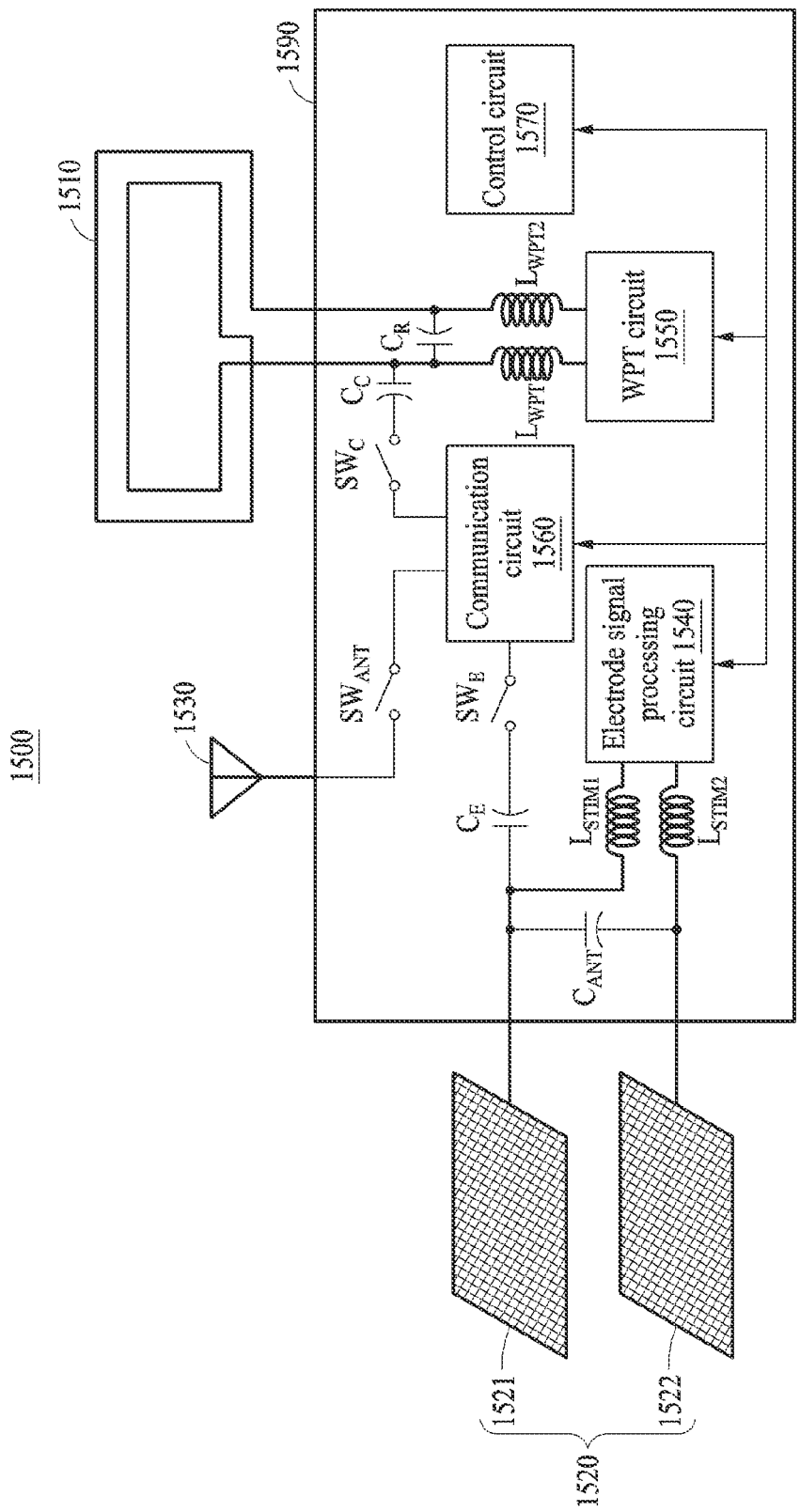
FIGS. 15 and 16 illustrate examples of an electronic apparatus including a coil, an electrode, and an antenna.
Figure 16:
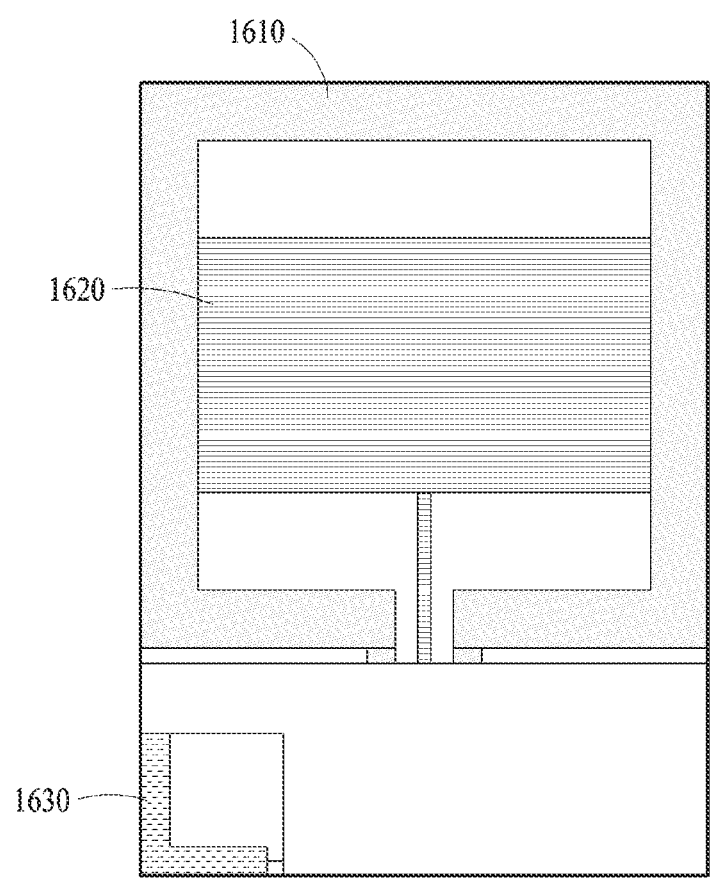

FIGS. 15 and 16 illustrate examples of an electronic apparatus including a coil, an electrode, and an antenna.

Referring to FIG. 15, an electronic apparatus 1500 may further include an external antenna 1530 that may be connected to a communication circuit 1560 in a circuit shown in FIG. 1, and may further include switches $SW_{ANT}$, $SW_C$, and $SW_E$ that selectively connect external elements and the communication circuit 1560. An external coil 1510, an electrode pair 1520 including a first electrode 1521 and a second electrode 1522, an electrode signal processing circuit 1540, a WPT circuit 1550, the communication circuit 1560, a control circuit 1570, and a housing 1590 may be the same as or similar to those corresponding components of FIG. 1.

In an example, the communication circuit 1560 may be connected to the external coil 1510, an external electrode (for example, the electrode pair 1520), and the external antenna 1530 via the switches $SW_{ANT}$, $SW_C$, and $SW_E$. The communication circuit 1560 may select an external element that exhibits highest communication performance among communication performance using the external coil 1510, communication performance using the external electrode, and communication performance using the external antenna 1530, and may perform a communication in a third frequency band. For example, the control circuit 1570 of the electronic apparatus 1500 may sequentially select external elements, may measure communication performance of each of the external elements, may select at least one external element that exhibits highest reception performance based on the measured communication performance, and may connect the at least one external element to the communication circuit 1560. Also, the control circuit 1570 may connect any one or any combination of two or more of the external coil 1510, the external electrode, and the external antenna 1530 to the communication circuit 1560 and may perform a wireless communication.

FIG. 16 illustrates an example of an implementation of the electronic apparatus 1500 of FIG. 15.

An external coil 1610 may have a size of 20 mm×20 mm, an external electrode 1620 may have a size of 17 mm×14.5 mm, and an external antenna 1630 may have a size of 5 mm×5 mm. A relatively small amount of power may be consumed by elements (for example, capacitors and inductors) for switching for each operating frequency band in each of the external coil 1610, the external electrode 1620, and the external antenna 1630, and an antenna gain loss may be minimized. Also, a radiation pattern of the external coil 1610, a radiation pattern of the external electrode 1620, and a radiation pattern of the external antenna 1630 may be complementary to each other.

Also, the electronic apparatus 1500 may perform a wireless communication using an electric field based on a monopole scheme or a dipole scheme, and may receive power using a magnetic field, and thus mutual interference between a wireless communication and a wireless power reception may be minimized.

FIGS. 17 to 20 illustrate examples of an electronic apparatus having a structure in which a coil and an electrode are integrated.

Figure 17:
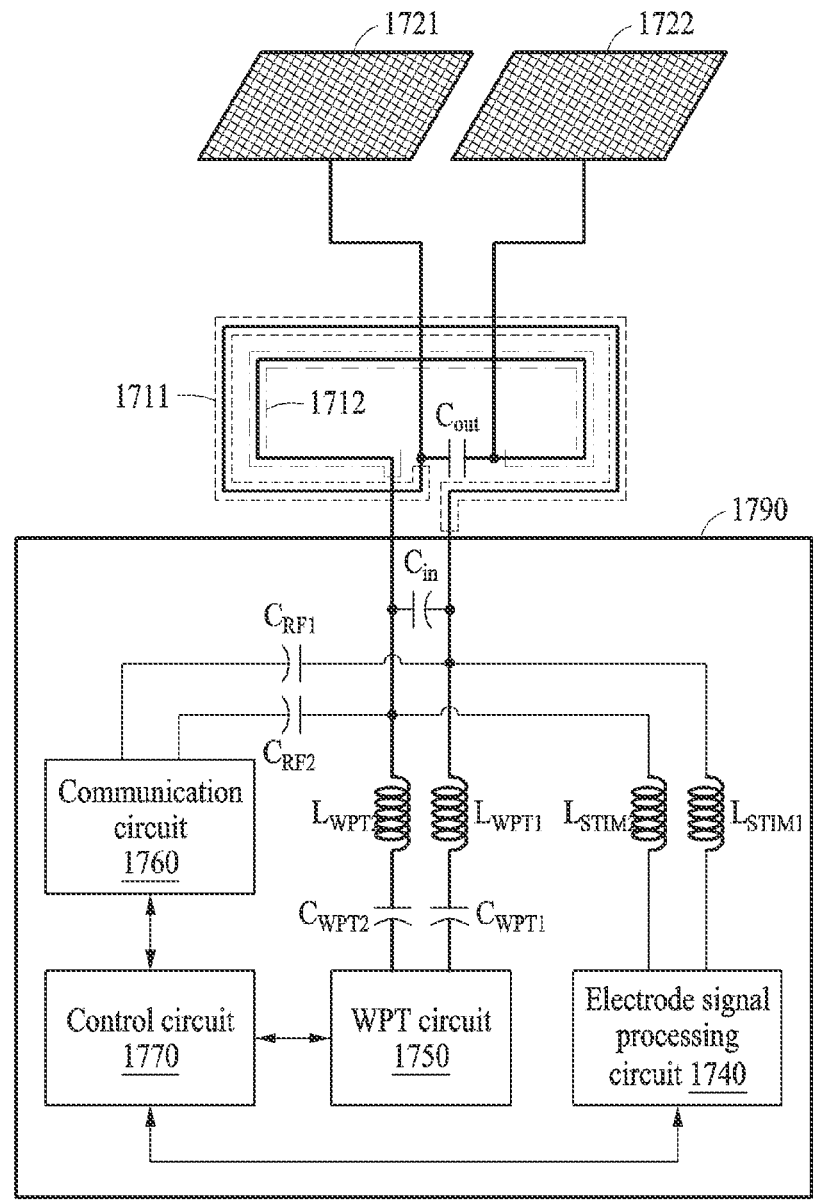
FIGS. 17 to 20 illustrate examples of an electronic apparatus having a structure in which a coil and an electrode are integrated.

FIG. 17 illustrates an electronic apparatus including an external antenna assembly in which an external electrode and an external coil are integrated.

The electronic apparatus may include the external coil, an external capacitor $C_{OUT}$, the external electrode, an electrode signal processing circuit 1740, a WPT circuit 1750, a communication circuit 1760, a control circuit 1770, and a housing 1790. The electrode signal processing circuit 1740, the WPT circuit 1750, the communication circuit 1760, the control circuit 1770, and the housing 1790 may be the same as those described above with reference to FIG. 1.

The external coil may include a first coil part 1711 and a second coil part 1712 disposed outside the housing 1790. The external coil may be connected to the communication circuit 1760, the WPT circuit 1750, and the electrode signal processing circuit 1740 via a single pair of feed-through portions. The first coil part 1711 may be connected in series between one end of the external capacitor $C_{OUT}$ and a first feed-through portion (for example, a first port) of the pair of the feed-through portions. The second coil part 1712 may be connected in series between another end of the external capacitor $C_{OUT}$ and a second feed-through portion (for example, a second port) of the pair of the feed-through portions. The first coil part 1711 and the second coil part 1712 may have equivalent impedance. For example, an impedance difference between the first coil part 1711 and the second coil part 1712 may be less than a threshold impedance. Thus, power fed through the feed-through portions may be evenly distributed to a portion corresponding to the first electrode 1721 and the first coil part 1711 and a portion corresponding to the second electrode 1722 and the second coil part 1712.

The external capacitor $C_{OUT}$ may be disposed outside the housing 1790 and may be connected between the first coil part 1711 and the second coil part 1712. One end of the first coil part 1711 and one end of the second coil part 1712 may be connected to the external capacitor $C_{OUT}$, and another end of the first coil part 1711 and one end of the second coil part 1712 may be connected to feed-through ports, respectively. The feed-through ports and the external coil may be sealed and molded to block a liquid access, similarly to the description of FIG. 1.

Figure 21:
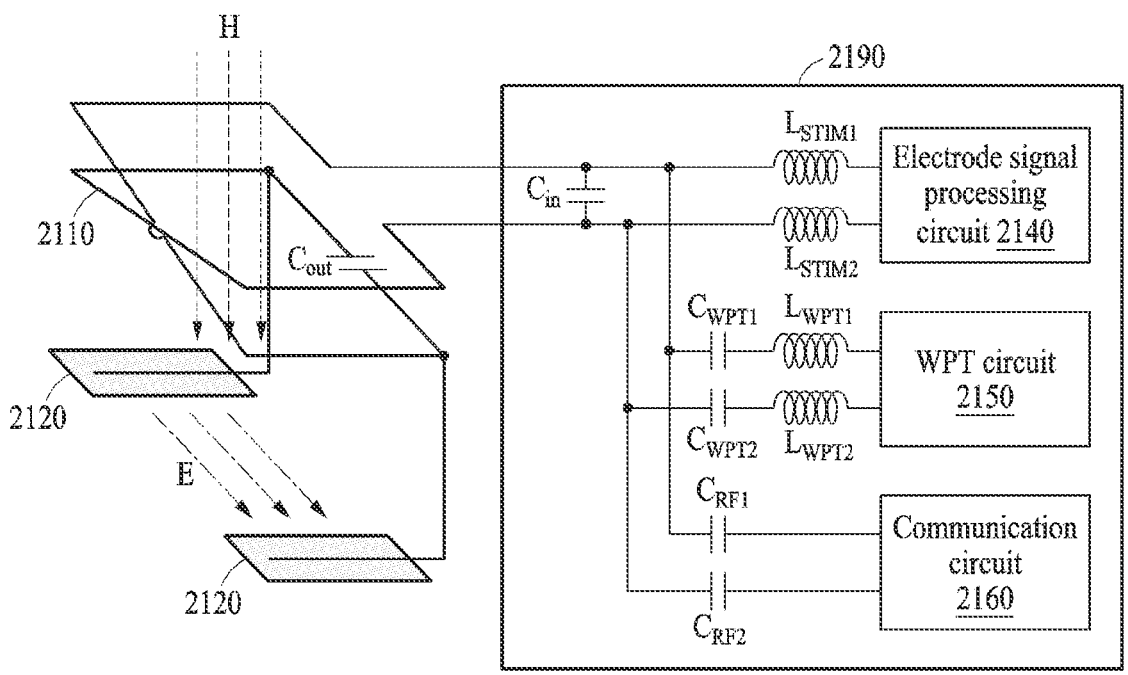
FIGS. 21 and 22 illustrate examples of a brain stimulator.

The external electrode may include the first electrode 1721 and the second electrode 1722. The first electrode 1721 may be connected to the first coil part 1711 at one end of the external capacitor $C_{OUT}$. The second electrode 1722 may be connected to the second coil part 1712 at another end of the external capacitor $C_{OUT}$. The external electrode may have a shape of a mesh as shown in FIG. 17, however, examples are not limited thereto. The external electrode may be implemented in various planar shapes, for example, a planar spiral shape, a planar spiral mesh shape, a planar polygonal shape, a planar circular shape, and a planar oval shape, and may also be implemented as a conducting line connected to an external coil as shown in FIG. 21.

In an example, the electrode signal processing circuit 1740 may be connected in series to both ends of the external coil via a pair of inductors. The electrode signal processing circuit 1740 may be connected to the first coil part 1711 via an inductor $L_{STIM1}$, and may be connected to the second coil part 1712 via an inductor $L_{STIM2}$. The electrode signal processing circuit 1740 may perform at least one of applying of an electrode signal to the first electrode 1721 and the second electrode 1722 and sensing of an electrode signal from the first electrode 1721 and the second electrode 1722. The inductors $L_{STIM1}$ and $L_{STIM2}$ connected to the electrode signal processing circuit 1740 may pass an electrode signal of a first frequency band and may block an electrode signal of the other frequency bands higher than the first frequency band, between the external coil and the electrode signal processing circuit 1740. The electrode signal may include, for example, a signal for an electrical stimulation, and/or an electric signal for sensing biometric information.

In an example, the WPT circuit 1750 may be connected in series to the external coil via a pair of combinations of inductors and capacitors. The WPT circuit 1750 may be connected to the first coil part 1711 via an inductor $L_{WPT1}$ and a capacitor $C_{WPT1}$ that are connected to each other in series, and may be connected to the second coil part 1712 via an inductor $L_{WPT2}$ and a capacitor $C_{WPT2}$ that are connected to each other in series. The WPT circuit 1750 may wirelessly receive power from an external device through the external coil according to a resonant frequency determined based on inductance of the external coil and inductance of an internal capacitor $C_{in}$. The internal capacitor $C_{in}$ may be connected to the ends of the external coil in parallel. In other words, the internal capacitor $C_{in}$ may be connected between a pair of feed-through ports in the housing 1790. A combination of the inductor $L_{WPT1}$ and a capacitor $C_{WPT1}$ that are connected to each other in series and a combination of the inductor $L_{WPT2}$ and a capacitor $C_{WPT2}$ that are connected to each other in series may receive power of a second frequency band between the first frequency band and a third frequency band and may block an electrode signal of the first frequency band and a communication signal of the third frequency band, between the external coil and the WPT circuit 1750.

In an example, the communication circuit 1760 may be connected to the external coil in series via a pair of capacitors. The communication circuit 1760 may be connected to the first coil part 1711 via a capacitor $C_{RF1}$ and may be connected to the second coil part 1712 via a capacitor $C_{RF2}$. The communication circuit 1760 may communicate with an external device using any one or any combination of the external coil, the first electrode 1721, and the second electrode 1722. The capacitors $C_{RF1}$ and $C_{RF2}$ connected to the communication circuit 1760 may block an electrode signal of the first frequency band and power of the second frequency band higher than the first frequency band and may pass a communication signal of the third frequency band higher than the second frequency band, between the external coil and the communication circuit 1760.

Thus, the electronic apparatus may perform three functions, for example, an electrode operation, a wireless power reception, and a wireless communication, using a single pair of feed-through. The electronic apparatus may perform a treatment function by applying an electrical stimulation through operating of an electrode, or may sense biometric information through the operating of the electrode. Also, the electronic apparatus may wirelessly receive power. The electronic apparatus may also establish a wireless communication with an external device. Operations of the electronic apparatus of FIG. 17 for each frequency band will be described below. As described above, for example, the first frequency band may include a frequency band of 0 Hz to 1 KHz, inclusive, the second frequency band may include a frequency band of 0.1 MHz to 20 MHz, inclusive, and the third frequency band may include a frequency band of 400 MHz to 10 GHz, inclusive.

Figure 18:
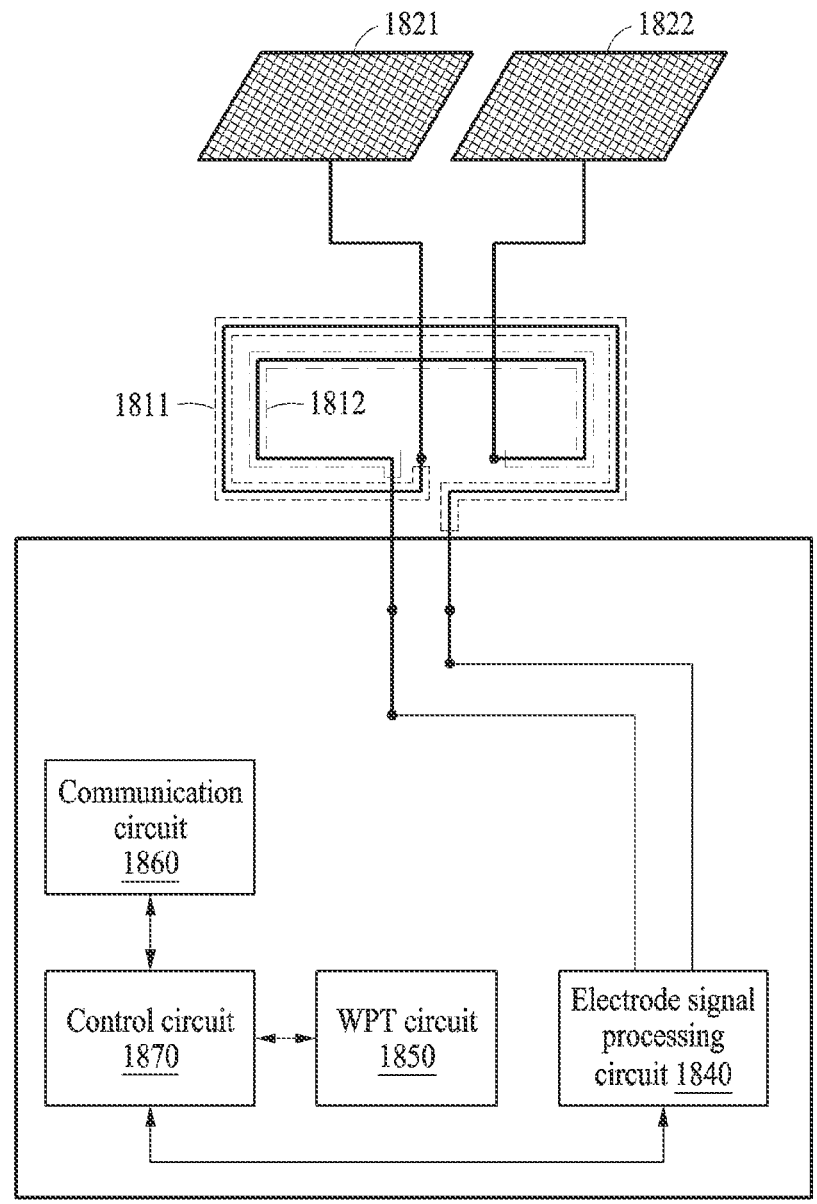

FIG. 18 illustrates an operation of a circuit of FIG. 17 in the first frequency band.

In the first frequency band, both ends of each of the inductors $L_{STIM1}$ and $L_{STIM2}$ may be shorted, and both ends of each of the capacitors $C_{WPT1}$, $C_{WPT2}$, $C_{RF1}$, and $C_{RF2}$ may be open. Also, both ends of each of the internal capacitor $C_{in}$ and the external capacitor $C_{out}$ may be open. In other words, a WPT circuit 1850 and a communication circuit 1860 may be disconnected from a first coil part 1811, a second coil part 1812, a first electrode 1821, and a second electrode 1822, and an electrode signal processing circuit 1840 may be connected to the first coil part 1811, the second coil part 1812, the first electrode 1821, and the second electrode 1822. Since the ends of the internal capacitor $C_{in}$ and the external capacitor $C_{out}$ are open, resonance by the first coil part 1811 and the second coil part 1812 may be prevented. The first coil part 1811 may connect the first electrode 1821 and the electrode signal processing circuit 1840 as a conducting line, and the second coil part 1812 may connect the second electrode 1822 and the electrode signal processing circuit 1840 as a conducting line. The electrode signal processing circuit 1840 may apply an electrode signal of the first frequency band to the first electrode 1821 and the second electrode 1822 based on a control of a control circuit 1870, or may sense an electrode signal of the first frequency band from the first electrode 1821 and the second electrode 1822.

Figure 19:
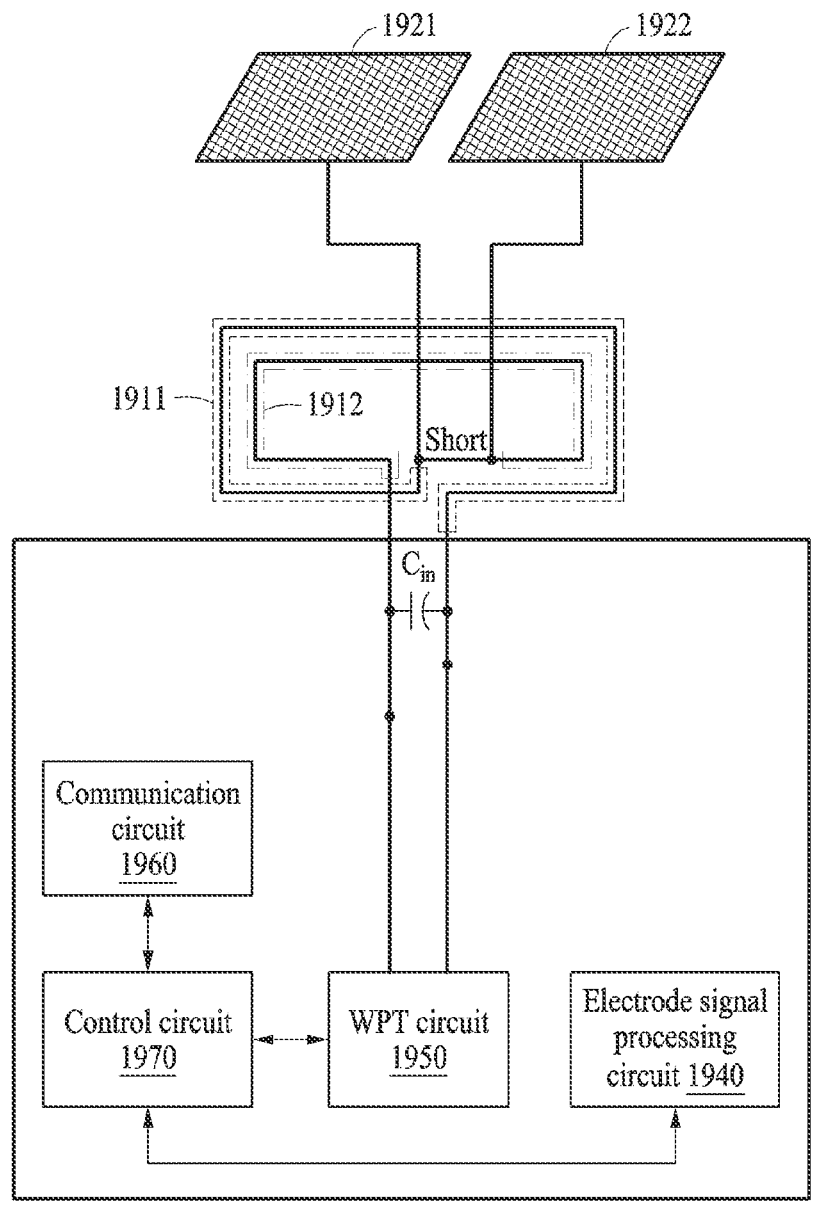

FIG. 19 illustrates an example of an operation of the circuit shown in FIG. 17 in the second frequency band.

In the second frequency band, the ends of the inductors $L_{STIM1}$ and $L_{STIM2}$ and the ends of the capacitors $C_{RF1}$, and $C_{RF2}$ may be open. Both ends of each of the inductor $L_{WPT1}$ and the capacitor $C_{WPT1}$ that are connected to each other in series and both ends of each of the inductor $L_{WPT2}$ and the capacitor $C_{WPT2}$ that are connected to each other in series may be shorted. Also, both ends of the external capacitor $C_{out}$ may be shorted. In addition, a resonant frequency may be formed by inductance of an external coil including a first coil part 1911 and a second coil part 1912 and capacitance of the internal capacitor $C_{in}$. For example, the resonant frequency may belong to the second frequency band.

In other words, an electrode signal processing circuit 1940 and a communication circuit 1960 may be disconnected from the first coil part 1911, the second coil part 1912, a first electrode 1921 and a second electrode 1922, and a WPT circuit 1950 may be connected to the first coil part 1911, the second coil part 1912, the first electrode 1921, and the second electrode 1922. Since the resonant frequency is formed by the inductance of the external coil and the capacitance of the internal capacitor $C_{in}$, the external coil may wirelessly receive power. The first electrode 1921 and the second electrode 1922 may not be involved in a wireless power reception operation or may have little influence on the wireless power reception operation. The WPT circuit 1950 may wirelessly receive power of the second frequency band via the external coil based on a control of a control circuit 1970.

Figure 20:
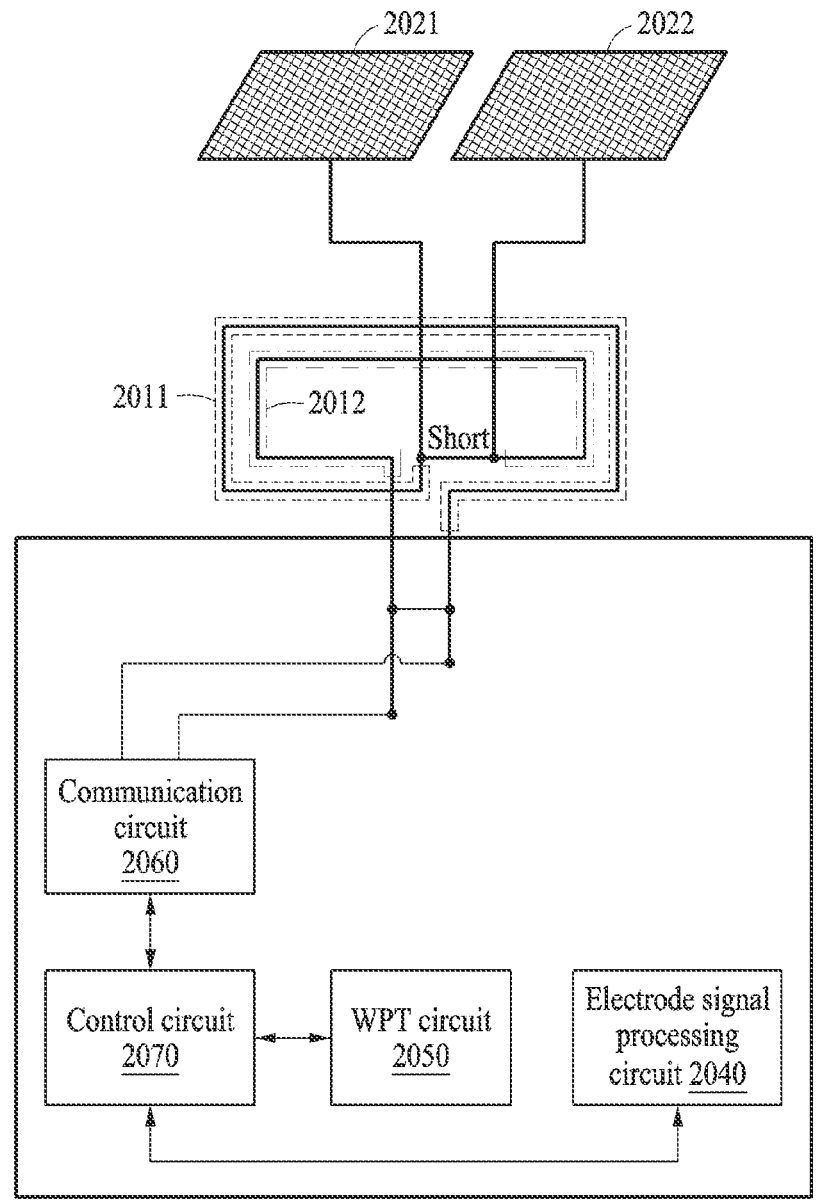

FIG. 20 illustrates an operation of the circuit of FIG. 17 in the third frequency band.

In the third frequency band, both ends of each of the inductors $L_{STIM1}$, $L_{STIM2}$, $L_{WPT1}$, and $L_{WPT2}$ may be open. Both ends of each of the capacitors $C_{RF1}$ and $C_{RF2}$, the external capacitor $C_{out}$ and the internal capacitor $C_{in}$ may be shorted.

In other words, an electrode signal processing circuit 2040 and a WPT circuit 2050 may be disconnected from a first coil part 2011, a second coil part 2012, a first electrode 2021, and a second electrode 2022, and a communication circuit 2060 may be connected to the first coil part 2011, the second coil part 2012, the first electrode 2021, and the second electrode 2022. Since the ends of the internal capacitor $C_{in}$ and the external capacitor $C_{out}$ are shorted, the first coil part 2011, the second coil part 2012, the first electrode 2021, and the second electrode 2022 may operate as an integrated metal conductor. The communication circuit 2060 may perform a wireless communication in the third frequency band by operating the first coil part 2011, the second coil part 2012, the first electrode 2021, and the second electrode 2022 that are integrally connected, as an antenna (for example, a monopole antenna) based on a control of a control circuit 2070.

All the first coil part 1711 and the second coil part 1712 of the external coil, the first electrode 1721, and the second electrode 1722 are connected to the communication circuit 1760 as shown in FIG. 17, however, examples are not limited thereto. Any one or any combination of two or more of the first coil part 1711, the second coil part 1712, the first electrode 1721, and the second electrode 1722 may be connected to the communication circuit 1760, and the communication circuit 1760 may operate a connected element and/or portion as a monopole antenna.

The electronic apparatus has a structure of a circuit that may perform all the electrical stimulation, the wireless power reception, and the wireless communication, and a power loss may not be significant compared to a circuit that is capable of performing an individual function alone. For example, the electronic apparatus may perform the above three functions using a single pair of feed-through portions, even in a wireless communication distance of 1 m. When the same amount of power is consumed by the electronic apparatus, a reduction in output power may be only 2% in comparison to a dedicated circuit for electrical stimulation. In the electronic apparatus, for the same transmitted power, a reduction in received power may be only 0.5% in comparison to a dedicated circuit for power reception.

Figure 22:
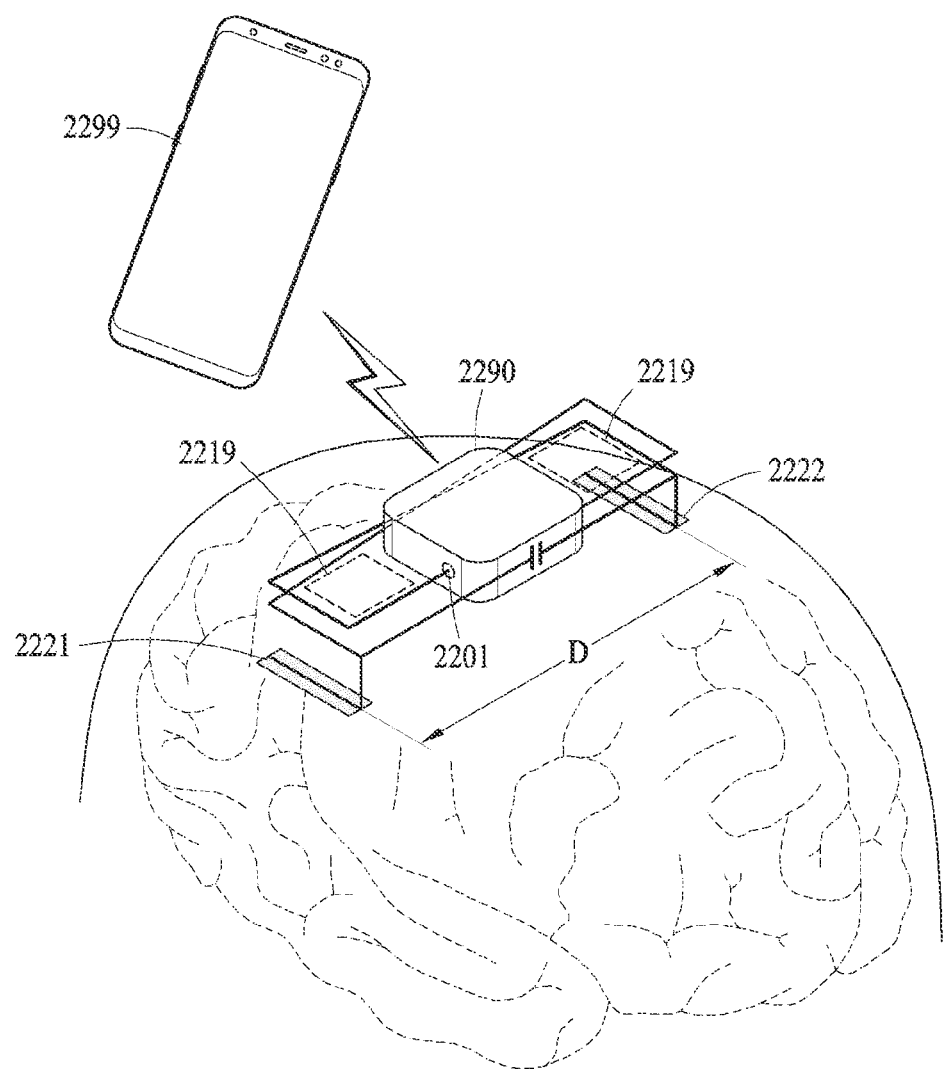

FIGS. 21 and 22 illustrate examples of a brain stimulator.

An electrode signal processing circuit 2140, a WPT circuit 2150, and a communication circuit 2160 may be connected to an external coil 2110 and an external electrode 2120, as described above with reference to FIGS. 17 to 20, and may be accommodated in a housing 2190. As shown in FIG. 21, a direction of a magnetic field H generated by the external coil 2110 during a wireless power reception operation, and a direction of an electric field E generated by the external electrode 2120 during an electrical stimulation operation may be perpendicular to each other. In other words, the magnetic field H generated by the external coil 2110 and the electric field E generated by the external electrode 2120 may not interfere with each other.

FIG. 22 illustrates an application example of an electronic apparatus of FIG. 21. An electronic apparatus of FIG. 22 may be, for example, a brain stimulator. The brain stimulator of FIG. 22 may be inserted into a region adjacent to a brain in a body of a user, for example, a skull of a head. However, a site in which the brain stimulator is implanted is not limited thereto.

An element and/or a circuit of the brain stimulator may be configured as described above with reference to FIGS. 17 to 21. The external coil 2110 and an external capacitor $C_{OUT}$ may be molded. For example, the external coil 2110 may be connected to circuits included in a housing 2290 through a pair of feed-through portions 2201 formed on both sides of the housing 2290, as shown in FIG. 22. The brain stimulator may establish a wireless communication with an external device 2299, or may wirelessly receive power. In an example, an area of an overlapping region between a plane region occupied by the external coil 2110 and a region occupied by the housing 2190 in a plane on which the external coil 2110 is disposed may be less than or equal to a first threshold area. An area of a region 2219 obtained by excluding a region occupied by the housing 2290 from the region occupied by the external coil 2110 in the plane on which the external coil 2110 is disposed may be greater than or equal to a second threshold area. When the housing 2290 is formed of metal, induction of a magnetic field may be limited in the region occupied by the housing 2290, and accordingly the brain stimulator may receive an amount of power proportional to the area of the region 2219.

A first electrode 2221 and a second electrode 2222 of the brain stimulator may be disposed on different sides of an external capacitor $C_{OUT}$ disposed outside the housing 2290. Both surfaces of each of the first electrode 2221 and the second electrode 2222 may be exposed, however, examples are not limited thereto. For example, one surface facing an object (for example, a brain) may be exposed and the other surface may be molded in the first electrode 2221 and the second electrode 2222. A distance D between the first electrode 2221 and the second electrode 2222 may be greater than or equal to a threshold distance. The first electrode 2221 and the second electrode 2222 may be spaced apart from each other by 2 cm or greater. The first electrode 2221 and the second electrode 2222 each have a shape of a conducting line as shown in FIG. 22, however, examples are not limited thereto.

FIGS. 23 to 26 illustrate examples of a bio-electroceutical device.

Figure 23:
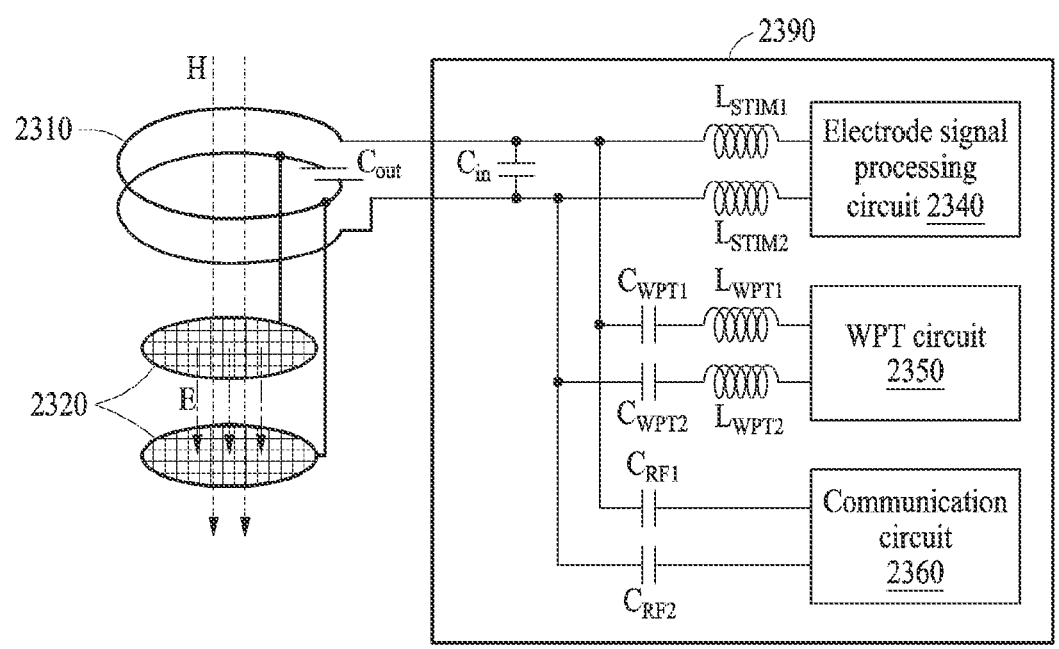
FIGS. 23 to 26 illustrate examples of a bio-electroceutical device.

An electrode signal processing circuit 2340, a WPT circuit 2350, and a communication circuit 2360 may be connected to an external coil 2310 and an external electrode 2320, as described above with reference to FIGS. 17 to 20, and may be accommodated in a housing 2390. As shown in FIG. 23, a direction of a magnetic field H generated by the external coil 2310 and a direction of an electric field E generated by the external electrode 2320 may be identical to each other. In other words, the magnetic field H generated by the external coil 2310 and the electric field E generated by the external electrode 2320 may not interfere with each other. A timing of generation of the magnetic field H and a timing of generation of the electric field E may not overlap, or overlapping between the timings may be minimized.

Figure 24:
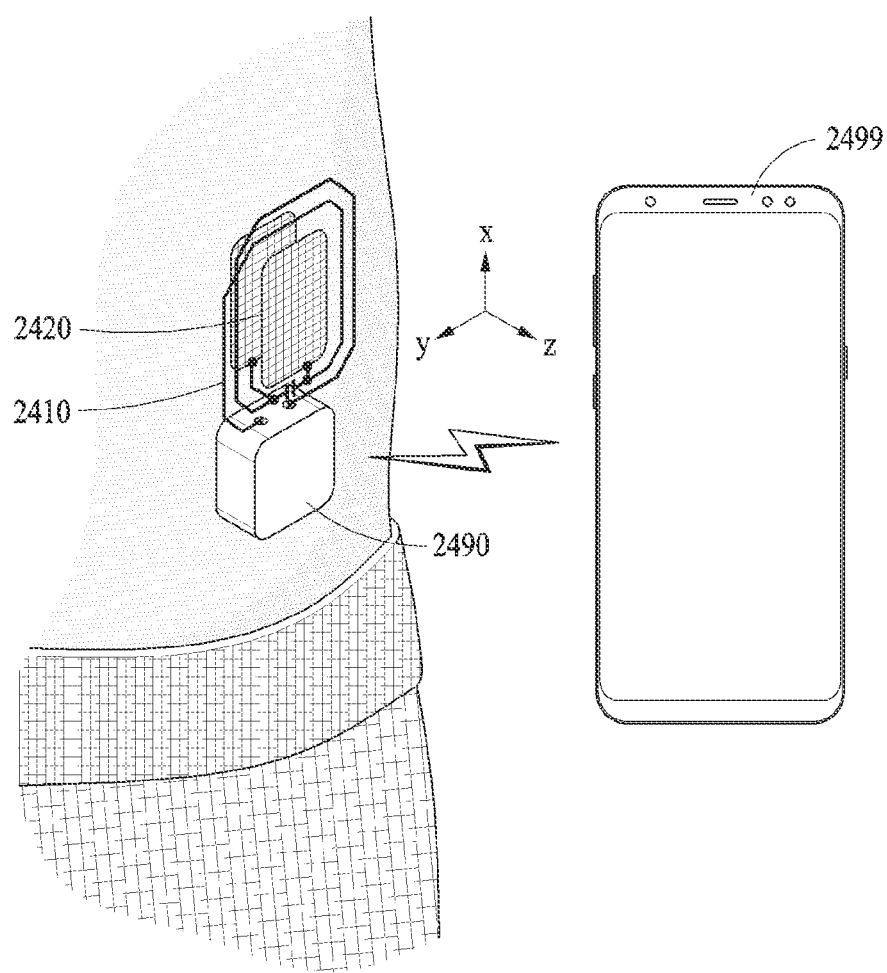

FIG. 24 illustrates an application example of an electronic apparatus of FIG. 23. An electronic apparatus of FIG. 24 may be, for example, a bio-electroceutical device. The bio-electroceutical device may operate as a type of artificial organs. The bio-electroceutical device of FIG. 24 may be inserted into a body of a user, for example, abdominal subcutaneous adipose tissues. However, a site in which the bio-electroceutical device is implanted is not limited thereto.

An element and/or a circuit of the bio-electroceutical device may be configured as described above with reference to FIGS. 17 to 20 and 23. An external coil 2410 and an external capacitor $C_{OUT}$ may be molded. The bio-electroceutical device may establish a wireless communication with an external device 2499, or may wirelessly receive power. In FIG. 24, a plane on which the external coil 2410 is disposed and a plane on which an external electrode 2420 is disposed may be parallel to each other, and are shown as x-y planes. An x-axis, a y-axis, and a z-axis may correspond to a length, a width, and a height of a housing 2490, respectively. However, an arrangement for minimization of a form factor is shown in FIG. 24, and an arrangement of the external coil 2410 and the external electrode 2420 is not limited thereto. A region occupied by the external coil 2410 does not overlap the housing 2490, and thus a wireless power reception efficiency by the external coil 2410 may be maximized.

Figure 25:
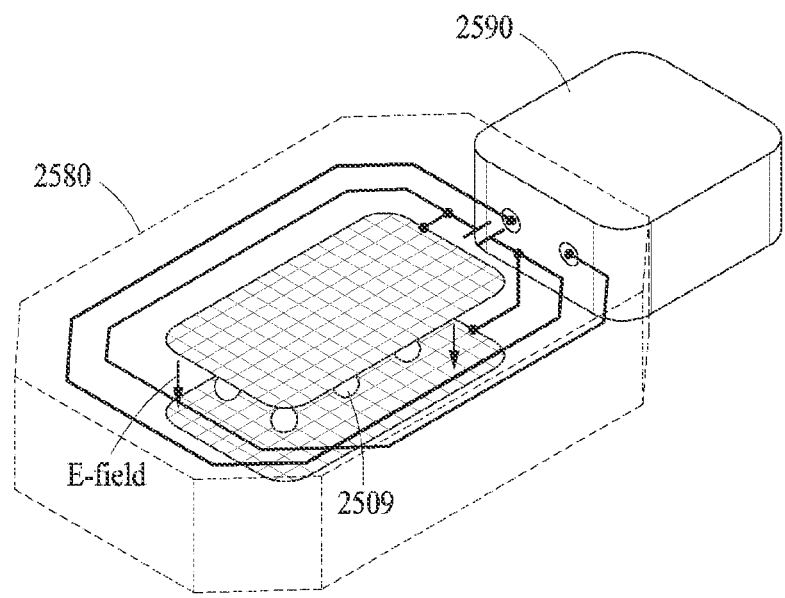
Figure 26:
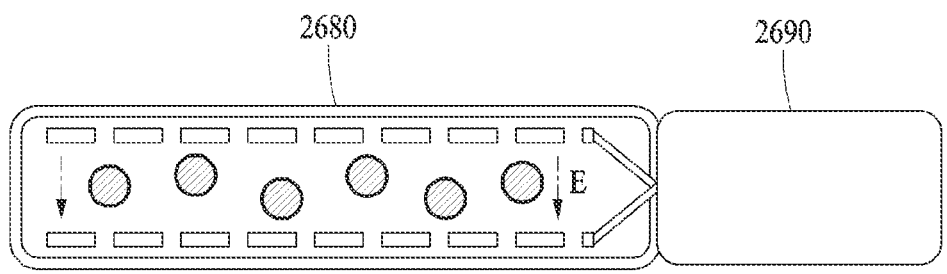

FIGS. 25 and 26 illustrate examples in which a bio-electroceutical device further includes a membrane. FIG. 25 is a perspective view of a bio-electroceutical device, and FIG. 26 is a cross-sectional view of a bio-electroceutical device.

The bio-electroceutical devices may further include membranes 2580 and 2680 that accommodate external electrodes exposed on one side of housings 2590 and 2690. The membranes 2580 and 2680 accommodate external coils as shown in FIG. 25, however, examples are not limited thereto. The external coils may be separately molded, and the membranes 2580 and 2680 may be disposed in spaces defined in the external coils.

The membranes 2580 and 2680 may accommodate beta cells 2509 together with the external electrodes, and may protect and maintain the beta cells 2509. The membranes 2580 and 2680 may be implemented as porous membranes. A porous membrane may include a plurality of pores having a diameter less than that of immune cells and greater than that of nutrients, may allow a flow of nutrients into the porous membrane and may prevent a flow of immune cells into the porous membrane through the plurality of pores.

In an example, a first electrode and a second electrode included in the external electrodes may be disposed on the same side based on the housings 2590 and 2690, and the beta cells 2509 disposed between the first electrode and the second electrode may provide electrode signals. The bio-electroceutical devices may facilitate secretion of insulin of the beta cells 2509 by applying an electrode signal (for example, an electric field E-field). However, an operation of an electrode is not limited thereto. The external electrodes may also be configured to sense a state of secretion of insulin and a concentration of glucose.

The electronic apparatuses, electrode signal processing circuits, WPT circuits, communication circuits, control circuits, external devices, and other apparatuses, devices, units, modules, and components described herein with respect to FIGS. 1-26 are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-26 that perform the operations described in this application are performed by computing hardware, for example, by one or more processors or computers, implemented as described above executing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions used herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD–Rs, CD+Rs, CD–RWs, CD+RWs, DVD-ROMs, DVD–Rs, DVD+Rs, DVD–RWs, DVD+RWs, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

Therefore, the scope of the disclosure is defined not by the detailed description, but by the claims and their equivalents, and all variations within the scope of the claims and their equivalents are to be construed as being included in the disclosure.

What is claimed is:

1. An electronic apparatus comprising:
an external coil connected via a pair of a first feed-through portion and a second feed-through portion to a communication circuit, the external coil comprising a first coil part and a second coil part disposed outside a housing;
a wireless power transmission circuit connected to the external coil;
an electrode signal processing circuit included in the housing and connected to the external coil;
an external capacitor disposed outside the housing and connected between the first coil part and the second coil part;
a first electrode connected to the first coil part at one end of the external capacitor; and
a second electrode connected to the second coil part at another end of the external capacitor.

2. The apparatus of claim 1, wherein
the first coil part is connected in series between the one end of the external capacitor and the first feed-through portion,
the second coil part is connected in series between the other end of the external capacitor and the second feed-through portion, and
the first coil part and second coil have equivalent impedance.

3. The apparatus of claim 1, wherein the electrode signal processing circuit is connected to the first coil part via an inductor, is connected to the second coil part via another inductor, and is configured to perform either one or both of applying of an electrode signal to the first electrode and the second electrode and sensing of an electrode signal from the first electrode and the second electrode.

4. The apparatus of claim 3, wherein the inductors connected to the electrode signal processing circuit are configured to pass an electrode signal of a first frequency band and to block an electrode signal of the other frequency bands higher than the first frequency band, between the external coil and the electrode signal processing circuit.

5. The apparatus of claim 1, wherein the wireless power transmission circuit is connected to the first coil part via an inductor and a capacitor that are connected in series to each other, is connected to the second coil part via another inductor and another capacitor that are connected in series to each other, and is configured to wirelessly receive power from an external device via the external coil.

6. The apparatus of claim 5, wherein a combination of the inductor and the capacitor that are connected in series to each other, and a combination of the other inductor and the other capacitor that are connected in series to each other receive power of a second frequency band between a first frequency band and a third frequency band and block an electrode signal of the first frequency band and a communication signal of the third frequency band, between the external coil and the wireless power transmission circuit.

7. The apparatus of claim 1, wherein the communication circuit is connected to the first coil part via a capacitor, is connected to the second coil part via another capacitor, and is configured to communicate with an external device using any one or any combination of the external coil, the first electrode, and the second electrode.

8. The apparatus of claim 7, wherein the capacitors connected to the communication circuit are configured to block an electrode signal of a first frequency band and power of a second frequency band higher than the first frequency band and to pass a communication signal of a third frequency band higher than the second frequency band, between the external coil and the communication circuit.

9. The apparatus of claim 1, wherein the first electrode and the second electrode are disposed on different sides of the external capacitor disposed outside the housing.

10. The apparatus of claim 9, wherein the first electrode and the second electrode are spaced apart from each other by 2 centimeters (cm) or greater.

11. The apparatus of claim 1, wherein an area of an overlapping region between a plane region occupied by the external coil and a region occupied by the housing in a plane on which the external coil is disposed is less than or equal to a threshold area.

12. The apparatus of claim 1, wherein the first electrode and the second electrode are disposed on a same side based on the housing and are configured to provide electrode signals to beta cells disposed between the first electrode and the second electrode.

13. An electronic apparatus, comprising:
an external element comprising an external coil and an external electrode disposed outside a housing, the external coil comprising a first coil part and a second coil part disposed outside the housing;
a communication circuit connected to the external element in series via a capacitor, configured to operate the external element as either one of a monopole antenna and a dipole antenna in a communication frequency band, and disposed inside the housing;
an additional circuit connected to the external element in series via an inductor and disposed inside the housing; and
an external capacitor disposed outside the housing and connected between the first coil part and the second coil part, the external capacitor comprising a first electrode connected to the first coil part at a first end of the external capacitor and a second electrode connected to the second coil part at a second end of the external capacitor,
wherein the external coil is connected via a pair of a first feed-through portion and a second feed-through portion to the communication circuit and the additional circuit.

14. The apparatus of claim 13, further comprising:
a first internal capacitor connected between both ends of the external coil,
wherein the additional circuit comprises a wireless power transmission circuit connected to the external coil in series via an inductor.

15. The apparatus of claim 13, wherein
the external electrode comprises a pair of a first electrode and a second electrode, and
the additional circuit comprises an electrode signal processing circuit connected to the first electrode in series via an inductor and connected to the second electrode in series via another inductor.

16. The apparatus of claim 15, further comprising:
a second internal capacitor connected between the first electrode and the second electrode.

17. The apparatus of claim 15, wherein
the first electrode is connected to the communication circuit in series via a capacitor, and
the second electrode is connected to the communication circuit in series via another capacitor.

18. The apparatus of claim 15, wherein
the first electrode is connected to the communication circuit in series via a capacitor and connected to the electrode signal processing circuit via an inductor, and
the second electrode is connected to a ground via another capacitor and connected to the electrode signal processing circuit.

19. The apparatus of claim 13, wherein
the communication circuit is connected to both the external coil and the external electrode, and is configured to select an external element that exhibits relatively high communication performance among communication performance using the external coil and communication performance using the external electrode, and to perform a communication.

20. The apparatus of claim 19, wherein the external element further comprises an external antenna connected to the communication circuit, and
wherein the communication circuit is connected to the external coil, the external electrode and the external antenna, and is configured to select an external element that exhibits highest communication performance among communication performance using the external coil, communication performance using the external electrode and communication performance using the external antenna, and to perform a communication.

21. An electronic apparatus, comprising:
an element including, the element being connected via a pair of a first feed-through portion and a second feed-through portion to a communication circuit and comprising a first coil part and a second coil part disposed outside a housing;
a capacitor configured to control transmission of an electrical signal between the coil and the communication circuit based on a frequency band of the electrical signal, the capacitor comprising a first electrode connected to the first coil part at a first end of the capacitor, and a second electrode connected to the second coil part at a second end of the capacitor; and
an inductor configured to control transmission of the electrical signal between the element and an additional circuit based on the frequency band,
wherein the coil is connected via a pair of a first feed-through portion and a second feed-through portion to the communication circuit and the additional circuit.

22. The apparatus of claim 21, wherein the capacitor is configured to:
pass the electrical signal between the element and the communication circuit, in response to the frequency band being a higher frequency band; and
block the electrical signal between the element and the communication circuit, in response to the frequency band being a lower frequency band.

23. The apparatus of claim 21, wherein the inductor is configured to:
pass the electrical signal between the element and the additional circuit, in response to the frequency band being a lower frequency band; and
block the electrical signal between the element and the additional circuit, in response to the frequency band being a higher frequency band.

24. The apparatus of claim 21, wherein the element further comprises an electrode, and
wherein the additional circuit comprises either one of:
a wireless power transmission circuit connected to the coil; and
an electrode signal processing circuit connected to the electrode.

* * * * *